(12) United States Patent
Kardailsky et al.

(10) Patent No.: US 7,626,082 B2
(45) Date of Patent: Dec. 1, 2009

(54) FLOWERING INDUCTION

(75) Inventors: Igor Kardailsky, Palmerston North (NZ); Bruce Edward Veit, Ashhurst (NZ); Natasha Talei Forester, Tokomaru (NZ); Milan Gagic, Palmerston North (NZ); Kim Archer Richardson, Palmerston North (NZ); Martin John Faville, Palmerston North (NZ); Gregory Thomas Bryan, Manawatu (NZ)

(73) Assignees: Agriculture Victoria Services Pty Ltd., Attwood (AU); AgResearch Limited, Hamilton (NZ)

( * ) Notice: Subject to any disclaimer, the term of this patent is extended or adjusted under 35 U.S.C. 154(b) by 156 days.

(21) Appl. No.: 10/557,032

(22) PCT Filed: May 14, 2004

(86) PCT No.: PCT/AU2004/000633

§ 371 (c)(1),
(2), (4) Date: Apr. 5, 2006

(87) PCT Pub. No.: WO2004/101791

PCT Pub. Date: Nov. 25, 2004

(65) Prior Publication Data

US 2008/0047029 A1 Feb. 21, 2008

(30) Foreign Application Priority Data

May 16, 2003 (AU) .............................. 2003902414

(51) Int. Cl.
C12N 15/29 (2006.01)
C12N 15/82 (2006.01)
C12N 5/04 (2006.01)
A01H 5/00 (2006.01)

(52) U.S. Cl. ...................... 800/298; 800/278; 800/290; 536/23.6; 536/24.1; 435/419; 435/320.1

(58) Field of Classification Search .................... None
See application file for complete search history.

(56) References Cited

U.S. PATENT DOCUMENTS 6,225,530 B1 * 5/2001 Weigel et al. ............... 800/290
2004/0088763 A1    5/2004 Yano et al.
2004/0126843 A1 * 7/2004 Demmer et al. ............ 435/69.1

FOREIGN PATENT DOCUMENTS

WO   WO 99/53070   10/1999
WO   WO 02/44390   6/2002

OTHER PUBLICATIONS

Armstead, I.P. "Synteny between a major heading-date QTL in perennial ryegrass (*Lolium perenne* L.) and the Hd3 heading-date locus rice" Jun. 18, 2003. pp. 822-828. Springer Verlag.
Kojima, Shoko. "Map-Based Cloning of the Rice Photoperiod Sensitivity QTL, Hd3A" Jan. 13-17, 2001 <http://www.intl-pag.org/9/abstracts/P02_40.html>.
Yano, Masahiro. "Genetic Control of Flowering Time in Rice, a Short-Day Plant" Dec. 2001. pp. 1425-1429 vol. 127. American Society of Plant Biologists.
Richardson Kim et al. "Microprojectile bombardment transformation of perennial ryegrass (*Lolium perenne*) for manipulation of flowering behaviour." In Vitro Cellular and Developmental Biology Animal. 2002. p. 80.A vol. 38, No. Abstract.
Izawa et al. "Phytochrome mediates the external light signal to repress FT orthologs in photoperiodic flowering of rice." Genes and Development, Cold Spring Harbor Laboratory Press. Aug. 1, 2002. pp. 2006-2020, vol. 16 No. 15.
Database EMBL. Citrus inshiu CiFT mRNA. May 28, 1999. Abstract XP002381263.
Database EMBL. Populus nigra PnFt3c mRNA for flowering locus T. Nov. 13, 2003. Abstract XP002381264.
Genbank Accession No. AAG31808:, A Terminal Flower1-like gene from perennial ryegrass involved in floral transition and axillary meristem identity, Jenson et al. Mar. 20, 2001.
Genbank Accession No. AAO31792: Comparative evolution of the SP/TFL1 gene family in tomato and *arabidopsis*, Carmel-Goren et al., Feb. 3, 2003.
Genbank Accession No. AB052944: Hd3a, a quantitative trait locus, involves in the promotion of flowering in rice, Kojima et al., Mar. 21, 2002.
Genbank Accession No. BAA77836: A pair of related genes with antagonistic roles in mediating flowering signals, Kobayashi et al., Feb. 26, 2000.
Genbank Accession No. BAB61027: Hd3a, a quanitative traitlocus, involves in the promotion of flowering in rice, Kojima et al., Mar. 21, 2002.

* cited by examiner

*Primary Examiner*—Stuart F. Baum
(74) *Attorney, Agent, or Firm*—Larson & Anderson, LLC

(57) ABSTRACT

The present invention relates to nucleic acids or nucleic acid fragments encoding amino acid sequences for proteins involved in the control of flowering in plants, and the use thereof for the modification of flowering in plants. In particular, the present invention relates to nucleic acids or nucleic acid fragments encoding amino acid sequences of FLOWERING LOCUS T (FT) polypeptides.

12 Claims, 14 Drawing Sheets

```
>rgft3.seq
AAAAAACTCATCAGCATCATCATTCATCCAGGTAGCTCCTGCTCCAGATCAATATACACCCTAGCTAAC
TAGCTCAGCTG
TGCCTGGTCATCGTCAACCTCTAGCTCCACCATACGAGATGGCCGGGAGGGATAGGGACCCGTTGGTGG
TTGGTAGGGTT
GTGGGGGATGTGCTGGACCCCTTCATCCGCACCACTAACCTCAGGGTGACATTCGGGAACCGGGCTGTG
TCCAACGGCTG
CGAGCTCAAGCCCTCCATGGTCACCCACCAGCCCAGGGTCGAGGTCGGCGGCAATGACATGAGGACCTT
CTACACACTCG
TGATGGTAGACCCCGACGCGCCAAGTCCAAGCGATCCCARCCTCAGAGAATACCTCCATTGGTTGGTGA
CAGATATTCCT
GGGACAACTGGTGCTTCCTTCGGGCAGGAGGTGATGTGCTACGAGAGCCCTCGCCCCAACATGGGGATC
CACCGCTTCGT
GCTCGTGCTCTTCCAGCAGCTGGGCCGGCAGACGGTGTACGCGCCCGGGTGGCGCCAGAACTTCAATAC
CAGGGACTTCG
CCGAGCTCTACAACCTCGGCCCGCCCGTCGCCGCCGTCTACTTCAACTGTCAGCGCGAGGCMGGCTCCG
GCGACAGGAGG
ATGTATAATTGACACCACCACAACAAGCCTCAGACCTACACAAGATCGATGATCCATTCACGGCGTGCC
TAGCTAAGCTT
AACTAATAATTACTATACTACATATGGTGTGTCATAAGAAGCTAGCTAGCCACGCAATTGATCAAGCAT
TATTTACACGC
ATAAAGATATATTGTGTACAACCTATATCATAACAATTATTAGCTACatatAAAAAAAAAAAAAAAGGC
TGCAGGGAATT
CAAGCTTACGCCAC
```

FIGURE 1

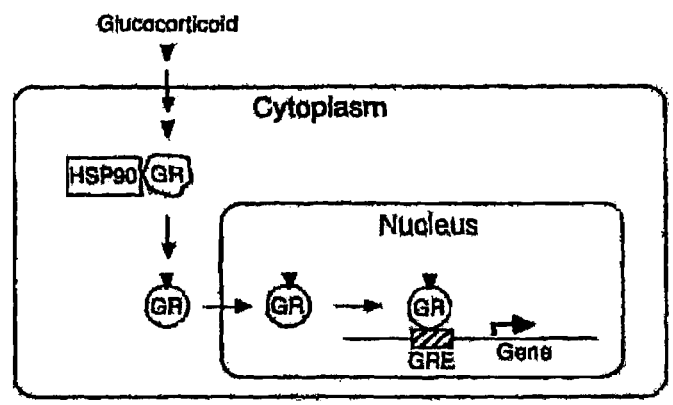
Activator
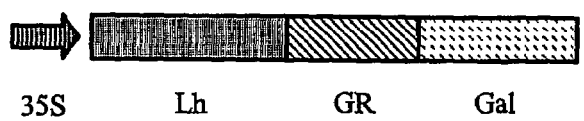
35S    Lh    GR    Gal
Reporter
35S    6XOP    35S    Reporter gene
FIGURE 4

FIGURE 6

SEQUENCE LISTING

```
<160> NUMBER OF SEQ ID NOS: 33

<210> SEQ ID NO 1
<211> LENGTH: 894
<212> TYPE: DNA
<213> ORGANISM: Lolium perenne

<400> SEQUENCE: 1
aaaaaactca tcagcatcat cattcatcca ggtagctcct gctccagatc aatatacacc      60
ctagctaact agctcagctg tgcctggtca tcgtcaacct ctagctccac catacgagat     120
ggccgggagg gatagggacc cgttggtggt tggtagggtt gtggggatg tgctggaccc     180 cttcatccgc accactaacc tcagggtgac attcgggaac cgggctgtgt ccaacggctg     240
cgagctcaag ccctccatgg tcacccacca gcccagggtc gaggtcggcg gcaatgacat     300
gaggaccttc tacacactcg tgatggtaga ccccgacgcg ccaagtccaa gcgatcccar     360
```

```
cctcagagaa tacctccatt ggttggtgac agatattcct gggacaactg gtgcttcctt    420
cgggcaggag gtgatgtgct acgagagccc tcgccccaac atggggatcc accgcttcgt    480
gctcgtgctc ttccagcagc tgggccggca gacggtgtac gcgcccgggt ggcgccagaa    540
cttcaatacc agggacttcg ccgagctcta caacctcggc ccgcccgtcg ccgccgtcta    600
cttcaactgt cagcgcgagg cmggctccgg cgacaggagg atgtataatt gacaccacca    660
caacaagcct cagacctaca caagatcgat gatccattca cggcgtgcct agctaagctt    720
aactaataat tactatacta catatggtgt gtcataagaa gctagctagc cacgcaattg    780
atcaagcatt atttacacgc ataaagatat attgtgtaca acctatatca taacaattat    840
tagctacata taaaaaaaaa aaaaaaggct gcagggaatt caagcttacg ccac          894
```

```
<210> SEQ ID NO 2
<211> LENGTH: 162
<212> TYPE: PRT
<213> ORGANISM: Arabidopsis thaliana

<400> SEQUENCE: 2

Asp Pro Leu Val Val Gly Arg Val Ile Gly Asp Val Leu Asp Met Phe
1               5                   10                  15

Ile Pro Thr Ala Asn Met Ser Val Tyr Phe Gly Pro Lys His Ile Thr
                20                  25                  30

Asn Gly Cys Glu Ile Lys Pro Ser Thr Ala Val Asn Pro Pro Lys Val
            35                  40                  45

Asn Ile Ser Gly His Ser Asp Glu Leu Tyr Thr Leu Val Met Thr Asp
        50                  55                  60

Pro Asp Ala Pro Ser Pro Ser Glu Pro Asn Met Arg Glu Trp Val His
65                  70                  75                  80

Trp Ile Val Val Asp Ile Pro Gly Gly Thr Asn Pro Ser Arg Gly Lys
                85                  90                  95

Glu Ile Leu Pro Tyr Met Glu Pro Arg Pro Val Gly Ile His Arg
                100                 105                 110

Tyr Ile Leu Val Leu Phe Arg Gln Asn Ser Pro Val Gly Leu Met Val
            115                 120                 125

Gln Gln Pro Pro Ser Arg Ala Asn Phe Ser Thr Arg Met Phe Ala Gly
        130                 135                 140

His Phe Asp Leu Gly Leu Pro Val Ala Thr Val Tyr Phe Asn Ala Gln
145                 150                 155                 160

Lys Glu

<210> SEQ ID NO 3
<211> LENGTH: 175
<212> TYPE: PRT
<213> ORGANISM: Arabidopsis thaliana

<400> SEQUENCE: 3

Met Ser Ile Asn Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
                20                  25                  30

Gly Gln Arg Glu Val Thr Asn Gly Leu Asp Leu Arg Pro Ser Gln Val
            35                  40                  45

Gln Asn Lys Pro Arg Val Glu Ile Gly Gly Glu Asp Leu Arg Asn Phe
        50                  55                  60

Tyr Thr Leu Val Met Val Asp Pro Asp Val Pro Ser Pro Ser Asn Pro
```

```
                65                  70                  75                  80
His Leu Arg Glu Tyr Leu His Trp Leu Val Thr Asp Ile Pro Ala Thr
                    85                  90                  95

Thr Gly Thr Thr Phe Gly Asn Glu Ile Val Cys Tyr Glu Asn Pro Ser
                100                 105                 110

Pro Thr Ala Gly Ile His Arg Val Phe Ile Leu Phe Arg Gln Leu
            115                 120                 125

Gly Arg Gln Thr Val Tyr Ala Pro Gly Trp Arg Gln Asn Phe Asn Thr
        130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 4
<211> LENGTH: 174
<212> TYPE: PRT
<213> ORGANISM: Arabidopsis thaliana

<400> SEQUENCE: 4

Met Ser Leu Ser Arg Arg Asp Pro Leu Val Gly Ser Val Val Gly
1               5                   10                  15

Asp Val Leu Asp Pro Phe Thr Arg Leu Val Ser Leu Lys Val Thr Tyr
                20                  25                  30

Gly His Arg Glu Val Thr Asn Gly Leu Asp Leu Arg Pro Ser Gln Val
            35                  40                  45

Leu Asn Lys Pro Ile Val Glu Ile Gly Gly Asp Phe Arg Asn Phe
    50                  55                  60

Tyr Thr Leu Val Met Val Asp Pro Asp Val Pro Ser Pro Ser Asn Pro
65                  70                  75                  80

His Gln Arg Glu Tyr Leu His Trp Leu Val Thr Asp Ile Pro Ala Thr
                85                  90                  95

Thr Gly Asn Ala Phe Gly Asn Glu Val Val Cys Tyr Glu Ser Pro Arg
                100                 105                 110

Pro Pro Ser Gly Ile His Arg Ile Val Leu Val Leu Phe Arg Gln Leu
            115                 120                 125

Gly Arg Gln Thr Val Tyr Ala Pro Gly Trp Arg Gln Phe Asn Thr
        130                 135                 140

Arg Glu Phe Ala Glu Ile Tyr Asn Leu Gly Leu Pro Val Ala Ala Ser
145                 150                 155                 160

Tyr Phe Asn Cys Gln Arg Glu Asn Gly Cys Gly Gly Arg Arg
                165                 170

<210> SEQ ID NO 5
<211> LENGTH: 174
<212> TYPE: PRT
<213> ORGANISM: Arabidopsis thaliana

<400> SEQUENCE: 5

Met Gly Thr Arg Val Ile Glu Pro Leu Ile Met Gly Arg Val Val Gly
1               5                   10                  15

Asp Val Leu Asp Phe Phe Thr Pro Thr Thr Lys Met Asn Val Ser Tyr
                20                  25                  30

Asn Lys Lys Gln Val Ser Asn Gly His Glu Leu Phe Pro Ser Ser Val
            35                  40                  45

Ser Ser Lys Pro Arg Val Glu Ile His Gly Gly Asp Leu Arg Ser Phe
```

```
                50                  55                  60
Phe Thr Leu Val Met Ile Asp Pro Asp Val Pro Gly Pro Ser Asp Pro
 65                  70                  75                  80

Phe Leu Lys Glu His Leu His Trp Ile Val Thr Asn Ile Pro Gly Thr
                     85                  90                  95

Thr Asp Ala Thr Phe Gly Lys Glu Val Val Ser Tyr Glu Leu Pro Arg
                100                 105                 110

Pro Ser Ile Gly Ile His Arg Phe Val Phe Val Leu Phe Arg Gln Lys
            115                 120                 125

Gln Arg Arg Val Ile Phe Pro Asn Ile Pro Ser Arg Asp His Phe Asn
130                 135                 140

Thr Arg Lys Phe Ala Val Glu Tyr Asp Leu Gly Leu Pro Val Ala Ala
145                 150                 155                 160

Val Phe Phe Asn Ala Gln Arg Glu Thr Ala Ala Arg Lys Arg
                165                 170

<210> SEQ ID NO 6
<211> LENGTH: 169
<212> TYPE: PRT
<213> ORGANISM: Arabidopsis thaliana

<400> SEQUENCE: 6

Asp Pro Leu Met Val Gly Arg Val Ile Gly Asp Val Val Asp Asn Cys
 1               5                  10                  15

Leu Gln Ala Val Lys Met Thr Val Thr Tyr Asn Ser Asp Lys Gln Val
                20                  25                  30

Tyr Asn Gly His Glu Leu Phe Pro Ser Val Val Thr Tyr Lys Pro Lys
            35                  40                  45

Val Glu Val His Gly Gly Asp Met Arg Ser Phe Phe Thr Leu Val Met
 50                  55                  60

Thr Asp Pro Asp Val Pro Gly Pro Ser Asp Pro Tyr Leu Arg Glu His
 65                  70                  75                  80

Leu His Trp Ile Val Thr Asp Ile Pro Gly Thr Thr Asp Val Ser Phe
                85                  90                  95

Gly Lys Glu Ile Ile Gly Tyr Glu Met Pro Arg Pro Asn Ile Gly Ile
            100                 105                 110

His Arg Phe Val Tyr Leu Leu Phe Lys Gln Thr Arg Arg Gly Ser Val
            115                 120                 125

Val Ser Val Pro Ser Tyr Arg Asp Gln Phe Asn Thr Arg Glu Phe Ala
130                 135                 140

His Glu Asn Asp Leu Gly Leu Pro Val Ala Ala Val Phe Phe Asn Cys
145                 150                 155                 160

Gln Arg Glu Thr Ala Ala Arg Arg Arg
                165

<210> SEQ ID NO 7
<211> LENGTH: 168
<212> TYPE: PRT
<213> ORGANISM: Lolium perenne

<400> SEQUENCE: 7

Glu Pro Leu Ile Val Gly Arg Val Ile Gly Glu Val Leu Asp Pro Phe
 1               5                  10                  15

Asn Pro Cys Val Lys Met Val Ala Thr Tyr Asn Ser Asn Lys Leu Val
                20                  25                  30

Phe Asn Gly His Glu Leu Tyr Pro Ser Ala Val Val Ser Lys Pro Arg
```

```
                35                  40                  45
Val Glu Val Gln Gly Gly Asp Leu Arg Ser Leu Phe Thr Leu Val Met
 50                  55                  60

Ala Asp Pro Asp Val Pro Gly Ser Asp Pro Tyr Leu Arg Glu His
 65                  70                  75                  80

Leu His Trp Ile Val Ser Asn Ile Pro Gly Thr Thr Asp Ala Ser Phe
                 85                  90                  95

Gly Gly Glu Val Met Ser Tyr Glu Ser Pro Lys Pro Asn Ile Gly Ile
                100                 105                 110

His Arg Phe Ile Phe Val Leu Phe Lys Gln Lys Arg Arg Gln Thr Val
                115                 120                 125

Ser Val Pro Ser Phe Arg Asp His Phe Asn Thr Arg Gln Phe Ala Val
                130                 135                 140

Asp Asn Asp Leu Gly Leu Pro Val Ala Ala Val Tyr Phe Asn Cys Gln
145                 150                 155                 160

Arg Glu Thr Ala Ala Arg Arg Arg
                165

<210> SEQ ID NO 8
<211> LENGTH: 164
<212> TYPE: PRT
<213> ORGANISM: Arabidopsis thaliana

<400> SEQUENCE: 8

Glu Pro Leu Ile Val Gly Arg Val Ile Gly Asp Val Leu Glu Met Phe
 1                5                  10                  15

Asn Pro Ser Val Thr Met Arg Val Thr Phe Asn Ser Asn Thr Ile Val
                 20                  25                  30

Ser Asn Gly His Glu Leu Ala Pro Ser Leu Leu Leu Ser Lys Pro Arg
                 35                  40                  45

Val Glu Ile Gly Gly Gln Asp Leu Arg Ser Phe Phe Thr Leu Ile Met
 50                  55                  60

Met Asp Pro Asp Ala Pro Ser Pro Ser Asn Pro Tyr Met Arg Glu Tyr
 65                  70                  75                  80

Leu His Trp Met Val Thr Asp Ile Pro Gly Thr Thr Asp Ala Ser Phe
                 85                  90                  95

Gly Arg Glu Ile Val Arg Tyr Glu Thr Pro Lys Pro Val Ala Gly Ile
                100                 105                 110

His Arg Tyr Val Phe Ala Leu Phe Lys Gln Arg Gly Arg Gln Ala Val
                115                 120                 125

Lys Ala Ala Pro Glu Thr Arg Glu Cys Phe Asn Thr Asn Ala Phe Ser
130                 135                 140

Ser Tyr Phe Gly Leu Ser Gln Pro Val Ala Ala Val Tyr Phe Asn Ala
145                 150                 155                 160

Gln Arg Glu Thr

<210> SEQ ID NO 9
<211> LENGTH: 72
<212> TYPE: PRT
<213> ORGANISM: Lolium perenne

<400> SEQUENCE: 9

Val Leu Tyr Leu Arg Pro Gln Pro Val Gly Ile His Arg Tyr Val
 1                5                  10                  15

Leu Val Leu Phe Gln Gln Lys Ser Arg Ile Val Asp Gly Tyr Ala Ala
                 20                  25                  30
```

```
Pro Pro Ala Asp Arg Pro Tyr Phe Asn Thr Arg Ala Phe Ala Phe Asn
            35                  40                  45

His Glu Leu Gly Leu Pro Val Ala Val Val Tyr Phe Asn Ser Gln Arg
 50                  55                  60

Glu Pro Ser Gly Asn Arg Arg
 65                  70

<210> SEQ ID NO 10
<211> LENGTH: 77
<212> TYPE: PRT
<213> ORGANISM: Lolium perenne

<400> SEQUENCE: 10

Val Ser Phe Gly Thr Glu Val Val Cys Tyr Glu Ser Pro Arg Pro Val
 1               5                  10                  15

Leu Gly Ile His Arg Leu Val Phe Leu Leu Phe Gln Gln Leu Gly Arg
            20                  25                  30

Gln Thr Val Tyr Ala Pro Gly Trp Arg Gln Asn Phe Ser Thr Arg Asp
            35                  40                  45

Phe Ala Glu Leu Tyr Asn Leu Gly Ser Pro Val Ala Ala Val Tyr Phe
 50                  55                  60

Asn Cys Gln Arg Glu Ser Gly Thr Gly Gly Arg Arg Met
 65                  70                  75

<210> SEQ ID NO 11
<211> LENGTH: 77
<212> TYPE: PRT
<213> ORGANISM: Lolium perenne

<400> SEQUENCE: 11

Val Ser Phe Gly Thr Glu Val Val Cys Tyr Glu Ser Pro Arg Pro Val
 1               5                  10                  15

Leu Gly Ile His Arg Leu Val Phe Leu Leu Phe Gln Gln Leu Gly Arg
            20                  25                  30

Gln Thr Val Tyr Ala Pro Gly Trp Arg Gln Asn Phe Ser Thr Arg Asp
            35                  40                  45

Phe Ala Glu Leu Tyr Asn Leu Gly Ser Pro Val Ala Ala Val Tyr Phe
 50                  55                  60

Asn Cys Gln Arg Glu Ser Gly Thr Gly Gly Arg Arg Met
 65                  70                  75

<210> SEQ ID NO 12
<211> LENGTH: 173
<212> TYPE: PRT
<213> ORGANISM: Lolium perenne

<400> SEQUENCE: 12

Met Ala Arg Val Val Glu Pro Leu Ile Val Gly Lys Val Ile Gly Glu
 1               5                  10                  15

Val Ile Asp Asn Phe Thr Pro Thr Glu Lys Met Thr Val Thr Tyr Ser
            20                  25                  30

Ser Asn Lys Gln Val Phe Asn Gly His Glu Phe Phe Pro Ser Ala Val
            35                  40                  45

Val Ser Lys Pro Arg Ile Glu Val Gln Gly Gly Asp Met Arg Ser Phe
 50                  55                  60

Phe Thr Leu Val Met Thr Asp Pro Asp Val Pro Gly Pro Ser Asp Pro
 65                  70                  75                  80
```

```
Tyr Leu Arg Glu His Leu His Trp Ile Val Asn Asn Ile Pro Gly Thr
                85                  90                  95

Thr Asp Ala Ser Phe Gly Lys Glu Val Val Ser Tyr Glu Ser Pro Lys
            100                 105                 110

Pro Asn Ile Gly Ile His Arg Phe Thr Phe Val Leu Phe Lys Gln Lys
        115                 120                 125

Gln Arg Gln Thr Met Ser Pro Pro Ser Ser Arg Asp Tyr Phe Asn Thr
    130                 135                 140

Arg Arg Phe Ala Ala Ala Asn Asp Leu Gly Leu Pro Val Ala Ala Val
145                 150                 155                 160

Tyr Phe Asn Ala Gln Arg Glu Thr Ala Ala Arg Arg
                165                 170
```

```
<210> SEQ ID NO 13
<211> LENGTH: 174
<212> TYPE: PRT
<213> ORGANISM: Lolium perenne

<400> SEQUENCE: 13

Met Ser Arg Ala Leu Glu Pro Leu Val Val Gly Lys Val Ile Gly Glu
1               5                   10                  15

Val Leu Asp Ser Phe Asn Pro Thr Val Lys Met Thr Ala Thr Tyr Ser
                20                  25                  30

Ser Asn Lys Gln Val Phe Asn Gly His Glu Phe Phe Pro Ser Ala Ile
            35                  40                  45

Ala Ala Lys Pro Arg Val Glu Val Gln Gly Gly Asp Leu Arg Ser Phe
        50                  55                  60

Phe Thr Leu Val Met Thr Asp Pro Asp Val Pro Gly Pro Ser Asp Pro
65                  70                  75                  80

Tyr Leu Arg Glu His Leu His Trp Ile Val Thr Asp Ile Pro Gly Thr
                85                  90                  95

Thr Asp Ala Ser Phe Gly Lys Glu Val Val His Tyr Glu Ser Pro Lys
            100                 105                 110

Pro Asn Ile Gly Ile His Arg Phe Ile Leu Val Leu Phe Gln Gln Thr
        115                 120                 125

His Arg Gly Ser Val Lys Asn Thr Pro Ser Ser Arg Asp Arg Phe Arg
    130                 135                 140

Thr Arg Glu Phe Ala Lys Asp Asn Glu Leu Gly Leu Pro Val Ala Ala
145                 150                 155                 160

Val Tyr Phe Asn Ala Gln Arg Glu Thr Ala Ala Arg Arg Arg
                165                 170
```

```
<210> SEQ ID NO 14
<211> LENGTH: 120
<212> TYPE: PRT
<213> ORGANISM: Lolium perenne

<400> SEQUENCE: 14

Met Thr Asp Pro Ala Ala Pro Ser Arg Lys Glu Pro Lys Phe Arg Glu
1               5                   10                  15

Trp His His Trp Leu Val Gly Asn Val Pro Glu Cys Asp Val Ala Lys
                20                  25                  30

Gly Glu Thr Leu Ser Glu Tyr Ile Gly Ser Gly Pro Pro Asp Thr
            35                  40                  45

Gly Leu His Arg Tyr Val Phe Leu Val Tyr Leu Gln Pro Gly Lys Ile
        50                  55                  60
```

```
Asp Phe Lys Asp Val Pro Arg Leu Thr Asn Arg Ser Gly Asp Asn Arg
 65                  70                  75                  80

Ala Asn Phe Lys Ile Gln Ala Phe Ala Asp Lys Tyr Asn Leu Gly Asp
                 85                  90                  95

Pro Val Ala Ser Ala Tyr Tyr Arg Ala Glu Tyr Asp Asp Tyr Val Pro
            100                 105                 110

Ile Leu Tyr Lys Gln Leu Gly Ala
        115                 120

<210> SEQ ID NO 15
<211> LENGTH: 176
<212> TYPE: PRT
<213> ORGANISM: Oryza sativa

<400> SEQUENCE: 15

Met Ser Gly Arg Gly Arg Gly Asp Pro Leu Val Leu Gly Arg Val Val
 1               5                  10                  15

Gly Asp Val Val Asp Pro Phe Val Arg Arg Val Ala Leu Arg Val Ala
                 20                  25                  30

Tyr Gly Ala Arg Glu Val Ala Asn Gly Cys Glu Leu Arg Pro Ser Ala
             35                  40                  45

Val Ala Asp Gln Pro Arg Val Ala Val Gly Gly Pro Asp Met Arg Thr
         50                  55                  60

Phe Tyr Thr Leu Val Met Val Asp Pro Asp Ala Pro Ser Pro Ser Asp
 65                  70                  75                  80

Pro Asn Leu Arg Glu Tyr Leu His Trp Leu Val Thr Asp Ile Pro Ala
                 85                  90                  95

Thr Thr Gly Val Ser Phe Gly Thr Glu Val Val Cys Tyr Glu Ser Pro
            100                 105                 110

Arg Pro Val Leu Gly Ile His Arg Leu Val Phe Leu Leu Phe Glu Gln
            115                 120                 125

Leu Gly Arg Gln Thr Val Tyr Ala Pro Gly Trp Arg Gln Asn Phe Ser
130                 135                 140

Thr Arg Asp Phe Ala Glu Leu Tyr Asn Leu Gly Leu Pro Val Ala Ala
145                 150                 155                 160

Val Tyr Phe Asn Cys Gln Arg Glu Ser Gly Thr Gly Gly Arg Arg Met
                165                 170                 175

<210> SEQ ID NO 16
<211> LENGTH: 178
<212> TYPE: PRT
<213> ORGANISM: Oryza sativa

<400> SEQUENCE: 16

Met Ser Gly Val Pro Thr Val Glu Pro Leu Val Leu Ala His Val Ile
 1               5                  10                  15

His Asp Val Leu Asp Pro Phe Pro Thr Met Pro Leu Arg Ile Thr
                 20                  25                  30

Tyr Asn Asp Arg Leu Leu Leu Ala Gly Ala Glu Leu Lys Pro Ser Ala
             35                  40                  45

Thr Val His Lys Pro Arg Val Asp Ile Gly Gly Thr Asp Leu Arg Val
         50                  55                  60

Phe Tyr Thr Leu Val Leu Val Asp Pro Asp Ala Pro Ser Pro Ser Asn
 65                  70                  75                  80

Pro Ser Leu Gly Glu Tyr Leu His Met Val Ile Asp Ile Pro Gly Thr
                 85                  90                  95
```

```
Thr Gly Val Asn Cys Gln Asp Leu Met Leu Tyr Glu Arg Pro Glu Leu
            100                 105                 110

Arg Tyr Gly Ile His Arg Met Val Phe Val Leu Phe Arg Gln Leu Gly
        115                 120                 125

Arg Gly Thr Val Phe Ala Pro Glu Met Arg His Asn Phe His Cys Arg
    130                 135                 140

Ser Phe Ala Gln Gln Tyr His Leu Asp Ile Val Ala Ala Thr Tyr Phe
145                 150                 155                 160

Asn Cys Gln Arg Glu Ala Gly Ser Gly Gly Arg Arg Phe Arg Ser Glu
                165                 170                 175

Ser Ser

<210> SEQ ID NO 17
<211> LENGTH: 173
<212> TYPE: PRT
<213> ORGANISM: Lolium perenne

<400> SEQUENCE: 17

Met Ser Arg Ser Val Glu Pro Leu Ile Val Gly Arg Val Ile Gly Glu
1               5                   10                  15

Val Leu Asp Pro Phe Asn Pro Cys Val Lys Met Val Ala Thr Tyr Asn
            20                  25                  30

Ser Asn Lys Leu Val Phe Asn Gly His Glu Leu Tyr Pro Ser Ala Val
        35                  40                  45

Val Ser Lys Pro Arg Val Glu Val Gln Gly Gly Asp Leu Arg Ser Leu
    50                  55                  60

Phe Thr Leu Val Met Thr Asp Pro Asp Val Pro Gly Pro Ser Asp Pro
65                  70                  75                  80

Tyr Leu Arg Glu His Leu His Trp Ile Val Ser Asn Ile Pro Gly Thr
                85                  90                  95

Thr Asp Ala Ser Phe Gly Gly Glu Val Met Ser Tyr Glu Ser Pro Lys
            100                 105                 110

Pro Asn Ile Gly Ile His Arg Phe Ile Phe Val Leu Phe Lys Gln Lys
        115                 120                 125

Arg Arg Gln Thr Val Ser Val Pro Ser Phe Arg Asp His Phe Asn Thr
    130                 135                 140

Arg Gln Phe Ala Val Asp Asn Asp Leu Gly Leu Pro Val Ala Ala Val
145                 150                 155                 160

Tyr Phe Asn Cys Gln Arg Glu Thr Ala Ala Arg Arg Arg
                165                 170

<210> SEQ ID NO 18
<211> LENGTH: 173
<212> TYPE: PRT
<213> ORGANISM: Oryza sativa

<400> SEQUENCE: 18

Met Ser Arg Ser Val Glu Pro Leu Val Val Gly Arg Val Ile Gly Glu
1               5                   10                  15

Val Ile Asp Ser Phe Asn Pro Cys Thr Lys Met Ile Val Thr Tyr Asn
            20                  25                  30

Ser Asn Lys Leu Val Phe Asn Gly His Glu Phe Tyr Pro Ser Ala Val
        35                  40                  45

Val Ser Lys Pro Arg Val Glu Val Gln Gly Gly Asp Met Arg Ser Phe
    50                  55                  60

Phe Thr Leu Val Met Thr Asp Pro Asp Val Pro Gly Pro Ser Asp Pro
```

```
                65                  70                  75                  80
Tyr Leu Arg Glu His Leu His Trp Ile Val Thr Asp Ile Pro Gly Thr
                    85                  90                  95

Thr Asp Ala Ser Phe Gly Arg Glu Ile Ile Ser Tyr Glu Ser Pro Lys
                100                 105                 110

Pro Ser Ile Gly Ile His Arg Phe Val Phe Val Leu Phe Lys Gln Lys
                115                 120                 125

Arg Arg Gln Ala Val Val Val Pro Ser Ser Arg Asp His Phe Asn Thr
    130                 135                 140

Arg Gln Phe Ala Glu Glu Asn Glu Leu Gly Leu Pro Val Ala Ala Val
145                 150                 155                 160

Tyr Phe Asn Ala Gln Arg Glu Thr Ala Ala Arg Arg
                165                 170
```

<210> SEQ ID NO 19
<211> LENGTH: 178
<212> TYPE: PRT
<213> ORGANISM: Oryza sativa

<400> SEQUENCE: 19

```
Met Ala Gly Ser Gly Arg Asp Asp Pro Leu Val Val Gly Arg Ile Val
1               5                   10                  15

Gly Asp Val Leu Asp Pro Phe Val Arg Ile Thr Asn Leu Ser Val Ser
                20                  25                  30

Tyr Gly Ala Arg Ile Val Ser Asn Gly Cys Glu Leu Lys Pro Ser Met
            35                  40                  45

Val Thr Gln Gln Pro Arg Val Val Gly Gly Asn Asp Met Arg Thr
    50                  55                  60

Phe Tyr Thr Leu Val Met Val Asp Pro Asp Ala Pro Ser Pro Ser Asn
65                  70                  75                  80

Pro Asn Leu Arg Glu Tyr Leu His Trp Leu Val Thr Asp Ile Pro Gly
                85                  90                  95

Thr Thr Gly Ala Thr Phe Gly Gln Glu Val Met Cys Tyr Glu Ser Pro
                100                 105                 110

Arg Pro Thr Met Gly Ile His Arg Leu Val Phe Val Leu Phe Gln Gln
                115                 120                 125

Leu Gly Arg Gln Thr Val Tyr Ala Pro Gly Trp Arg Gln Asn Phe Ser
    130                 135                 140

Thr Arg Asn Phe Ala Glu Leu Tyr Asn Leu Gly Ser Pro Val Ala Thr
145                 150                 155                 160

Val Tyr Phe Asn Cys Gln Arg Glu Ala Gly Ser Gly Arg Arg Val
                165                 170                 175

Tyr Pro
```

<210> SEQ ID NO 20
<211> LENGTH: 180
<212> TYPE: PRT
<213> ORGANISM: Oryza sativa

<400> SEQUENCE: 20

```
Met Ser Ser Ala Asn Ser Leu Val Leu Gly Arg Val Ile Gly Asp Val
1               5                   10                  15

Val Asp Leu Phe Ser Pro Glu Val Thr Leu Arg Val Met Tyr Asn Gly
                20                  25                  30

Val Arg Val Val Asn Gly Glu Asp Leu Arg Pro Ser Ala Val Ser Ala
            35                  40                  45
```

Arg Pro Ser Val Glu Val Gly Gly Asp Leu His Gln Phe Tyr Thr Ile
    50                  55                  60

Val Met Val Asp Pro Asp Ala Pro Asn Pro Ser Asn Pro Thr Leu Arg
65                  70                  75                  80

Glu Tyr Leu His Trp Leu Val Thr Asp Ile Pro Gly Thr Thr Asp Ala
                85                  90                  95

Asn Tyr Gly Arg Glu Val Val Cys Tyr Glu Ser Pro Arg Pro Ala Ala
            100                 105                 110

Gly Ile His Arg Val Ala Val Leu Phe Arg Gln Met Ala Arg Gly
            115                 120                 125

Gly Val Asp Gln Pro Pro Leu Leu Arg His Asn Phe Ser Thr Arg Gly
    130                 135                 140

Phe Ala Asp Asp His Ala Leu Gly Ala Pro Val Ala Ala Ala Phe Phe
145                 150                 155                 160

Thr Cys Lys Pro Glu Gly Gly Thr Gly Gly Arg Arg Phe Arg Pro Pro
                165                 170                 175

Ser Arg His Ser
            180

<210> SEQ ID NO 21
<211> LENGTH: 173
<212> TYPE: PRT
<213> ORGANISM: Oryza sativa

<400> SEQUENCE: 21

Met Ser Arg Ser Val Glu Pro Leu Val Val Gly Arg Val Ile Gly Glu
1               5                   10                  15

Val Leu Asp Thr Phe Asn Pro Cys Met Lys Met Ile Val Thr Tyr Asn
                20                  25                  30

Ser Asn Lys Leu Val Phe Asn Gly His Glu Leu Tyr Pro Ser Ala Val
            35                  40                  45

Val Ser Lys Pro Arg Val Glu Val Gln Gly Gly Asp Leu Arg Ser Phe
    50                  55                  60

Phe Thr Leu Val Met Thr Asp Pro Asp Val Gly Pro Ser Asp Pro
65                  70                  75                  80

Tyr Leu Arg Glu His Leu His Trp Ile Val Thr Asp Ile Pro Gly Thr
                85                  90                  95

Thr Asp Ala Ser Phe Gly Arg Glu Val Ile Ser Tyr Glu Ser Pro Lys
            100                 105                 110

Pro Asn Ile Gly Ile His Arg Phe Ile Phe Val Leu Phe Lys Gln Lys
            115                 120                 125

Arg Arg Gln Thr Val Ile Val Pro Ser Phe Arg Asp His Phe Asn Thr
    130                 135                 140

Arg Arg Phe Ala Glu Glu Asn Asp Leu Gly Leu Pro Val Ala Ala Val
145                 150                 155                 160

Tyr Phe Asn Ala Gln Arg Glu Thr Ala Ala Arg Arg Arg
                165                 170

<210> SEQ ID NO 22
<211> LENGTH: 174
<212> TYPE: PRT
<213> ORGANISM: Oryza sativa

<400> SEQUENCE: 22

Met Ala Arg Phe Val Asp Pro Leu Val Val Gly Arg Val Ile Gly Glu
1               5                   10                  15

Val Val Asp Leu Phe Val Pro Ser Ile Ser Met Thr Ala Ala Tyr Gly
            20                  25                  30

Asp Arg Asp Ile Ser Asn Gly Cys Leu Val Arg Pro Ser Ala Ala Asp
        35                  40                  45

Tyr Pro Pro Leu Val Arg Ile Ser Gly Arg Arg Asn Asp Leu Tyr Thr
    50                  55                  60

Leu Ile Met Thr Asp Pro Asp Ala Pro Ser Pro Ser Asp Pro Ser Met
65                  70                  75                  80

Arg Glu Phe Leu His Trp Ile Val Val Asn Ile Pro Gly Gly Thr Asp
                85                  90                  95

Ala Ser Lys Gly Glu Glu Met Val Gly Tyr Met Gly Pro Arg Pro Thr
            100                 105                 110

Val Gly Ile His Arg Tyr Val Leu Val Leu Tyr Glu Gln Lys Ala Arg
        115                 120                 125

Phe Val Asp Gly Ala Leu Met Pro Pro Ala Asp Arg Pro Asn Phe Asn
    130                 135                 140

Thr Arg Ala Phe Ala Ala Tyr His Gln Leu Gly Leu Pro Thr Ala Val
145                 150                 155                 160

Val His Phe Asn Ser Gln Arg Glu Pro Ala Asn Arg Arg Arg
                165                 170

<210> SEQ ID NO 23
<211> LENGTH: 173
<212> TYPE: PRT
<213> ORGANISM: Oryza sativa

<400> SEQUENCE: 23

Met Ser Arg Val Leu Glu Pro Leu Val Val Gly Lys Val Ile Gly Glu
1               5                   10                  15

Val Ile Asp Asn Phe Asn Pro Thr Val Lys Met Thr Ala Thr Tyr Ser
            20                  25                  30

Ser Asn Lys Gln Val Phe Asn Gly His Glu Leu Phe Pro Ser Ala Val
        35                  40                  45

Val Ser Lys Pro Arg Val Glu Val Gln Gly Gly Asp Leu Arg Ser Phe
    50                  55                  60

Phe Thr Leu Val Met Thr Asp Pro Asp Val Pro Gly Pro Ser Asp Pro
65                  70                  75                  80

Tyr Leu Arg Glu His Leu His Trp Ile Val Thr Asp Ile Pro Gly Thr
                85                  90                  95

Thr Asp Ala Ser Phe Gly Arg Glu Val Val Ser Tyr Glu Ser Pro Lys
            100                 105                 110

Pro Asn Ile Gly Ile His Arg Phe Val Leu Val Leu Phe Lys Gln Lys
        115                 120                 125

Arg Arg Gln Ala Val Thr Pro Pro Ser Ser Arg Asp Tyr Phe Ser Thr
    130                 135                 140

Arg Arg Phe Ala Ala Asp Asn Asp Leu Gly Leu Pro Val Ala Ala Val
145                 150                 155                 160

Tyr Phe Asn Ala Gln Arg Glu Thr Ala Ala Arg Arg Arg
                165                 170

<210> SEQ ID NO 24
<211> LENGTH: 185
<212> TYPE: PRT
<213> ORGANISM: Oryza sativa

<400> SEQUENCE: 24

Met Ala Asn Asp Ser Leu Ala Thr Gly Arg Val Ile Gly Asp Val Leu
1               5                   10                  15

Asp Pro Phe Ile Ser Thr Val Asp Leu Thr Val Met Tyr Gly Asp Asp
            20                  25                  30

Gly Met Pro Val Ile Ser Gly Val Glu Leu Arg Ala Pro Ala Val Ala
        35                  40                  45

Glu Lys Pro Val Val Glu Val Gly Asp Asp Leu Arg Val Ala Tyr
    50                  55                  60

Thr Leu Val Met Val Asp Pro Asp Ala Pro Asn Pro Ser Asn Pro Thr
65                  70                  75                  80

Leu Arg Glu Tyr Leu His Trp Met Val Thr Asp Ile Pro Ala Ser Thr
                85                  90                  95

Asp Ala Thr Tyr Gly Arg Glu Val Val Cys Tyr Glu Ser Pro Asn Pro
            100                 105                 110

Thr Thr Gly Ile His Arg Met Val Leu Val Leu Phe Arg Gln Leu Gly
            115                 120                 125

Arg Glu Thr Val Tyr Ala Pro Ala Val Arg His Asn Phe Thr Thr Arg
    130                 135                 140

Ala Phe Ala Arg Arg Tyr Asn Leu Gly Ala Pro Val Ala Ala Val Tyr
145                 150                 155                 160

Phe Asn Cys Gln Arg Gln Ala Gly Ser Gly Gly Arg Arg Phe Thr Gly
                165                 170                 175

Pro Tyr Thr Ser Arg Arg Arg Gln Ala
            180                 185

<210> SEQ ID NO 25
<211> LENGTH: 179
<212> TYPE: PRT
<213> ORGANISM: Oryza sativa

<400> SEQUENCE: 25

Met Ala Gly Ser Gly Arg Asp Arg Asp Pro Leu Val Val Gly Arg Val
1               5                   10                  15

Val Gly Asp Val Leu Asp Ala Phe Val Arg Ser Thr Asn Leu Lys Val
            20                  25                  30

Thr Tyr Gly Ser Lys Thr Val Ser Asn Gly Cys Glu Leu Lys Pro Ser
            35                  40                  45

Met Val Thr His Gln Pro Arg Val Glu Val Gly Gly Asn Asp Met Arg
    50                  55                  60

Thr Phe Tyr Thr Leu Val Met Val Asp Pro Asp Ala Pro Ser Pro Ser
65                  70                  75                  80

Asp Pro Asn Leu Arg Glu Tyr Leu His Trp Leu Val Thr Asp Ile Pro
                85                  90                  95

Gly Thr Thr Ala Ala Ser Phe Gly Gln Glu Val Met Cys Tyr Glu Ser
            100                 105                 110

Pro Arg Pro Thr Met Gly Ile His Arg Leu Val Phe Val Leu Phe Gln
    115                 120                 125

Gln Leu Gly Arg Gln Thr Val Tyr Ala Pro Gly Trp Arg Gln Asn Phe
130                 135                 140

Asn Thr Lys Asp Phe Ala Glu Leu Tyr Asn Leu Gly Ser Pro Val Ala
145                 150                 155                 160

Ala Val Tyr Phe Asn Cys Gln Arg Glu Ala Gly Ser Gly Gly Arg Arg
                165                 170                 175

Val Tyr Pro

```
<210> SEQ ID NO 26
<211> LENGTH: 177
<212> TYPE: PRT
<213> ORGANISM: Lolium perenne

<400> SEQUENCE: 26

Met Ala Gly Arg Asp Arg Asp Pro Leu Val Val Gly Arg Val Val Gly
1               5                   10                  15

Asp Val Leu Asp Pro Phe Ile Arg Thr Thr Asn Leu Arg Val Thr Phe
                20                  25                  30

Gly Asn Arg Ala Val Ser Asn Gly Cys Glu Leu Lys Pro Ser Met Val
            35                  40                  45

Thr His Gln Pro Arg Val Glu Val Gly Gly Asn Asp Met Arg Thr Phe
        50                  55                  60

Tyr Thr Leu Val Met Val Asp Pro Asp Ala Pro Ser Pro Ser Asp Pro
65                  70                  75                  80

Asn Leu Arg Glu Tyr Leu His Trp Leu Val Thr Asp Ile Pro Gly Thr
                85                  90                  95

Thr Gly Ala Ser Phe Gly Gln Glu Val Met Cys Tyr Glu Ser Pro Arg
            100                 105                 110

Pro Asn Met Gly Ile His Arg Phe Val Leu Val Leu Phe Gln Gln Leu
        115                 120                 125

Gly Arg Gln Thr Val Tyr Ala Pro Gly Trp Arg Gln Asn Phe Asn Thr
    130                 135                 140

Arg Asp Phe Ala Glu Leu Tyr Asn Leu Gly Pro Pro Val Ala Ala Val
145                 150                 155                 160

Tyr Phe Asn Cys Gln Arg Glu Ala Gly Ser Gly Asp Arg Arg Met Tyr
                165                 170                 175

Asn

<210> SEQ ID NO 27
<211> LENGTH: 177
<212> TYPE: PRT
<213> ORGANISM: Lolium perenne

<400> SEQUENCE: 27

Met Ala Gly Arg Asp Arg Asp Pro Leu Val Val Gly Arg Val Val Gly
1               5                   10                  15

Asp Val Leu Asp Pro Phe Ile Arg Thr Thr Asn Leu Arg Val Thr Phe
                20                  25                  30

Gly Asn Arg Ala Val Ser Asn Gly Cys Glu Leu Lys Pro Ser Met Val
            35                  40                  45

Thr His Gln Pro Arg Val Glu Val Gly Gly Asn Asp Met Arg Thr Phe
        50                  55                  60

Tyr Thr Leu Val Met Val Asp Pro Asp Ala Pro Ser Pro Ser Asp Pro
65                  70                  75                  80

Ser Leu Arg Glu Tyr Leu His Trp Leu Val Thr Asp Ile Pro Gly Thr
                85                  90                  95

Thr Gly Ala Ser Phe Gly Gln Glu Val Met Cys Tyr Glu Ser Pro Arg
            100                 105                 110

Pro Asn Met Gly Ile His Arg Phe Val Leu Val Leu Phe Gln Gln Leu
        115                 120                 125

Gly Arg Gln Thr Val Tyr Ala Pro Gly Trp Arg Gln Asn Phe Asn Thr
    130                 135                 140
```

```
Arg Asp Phe Ala Glu Leu Tyr Asn Leu Gly Pro Pro Val Ala Val
145                 150                 155                 160

Tyr Phe Asn Cys Gln Arg Glu Ala Gly Ser Gly Asp Arg Arg Met Tyr
                165                 170                 175

Asn

<210> SEQ ID NO 28
<211> LENGTH: 23
<212> TYPE: DNA
<213> ORGANISM: Artificial
<220> FEATURE:
<223> OTHER INFORMATION: synthetic primer

<400> SEQUENCE: 28
gctgttttcc ctagcattgt tgg                                        23

<210> SEQ ID NO 29
<211> LENGTH: 23
<212> TYPE: DNA
<213> ORGANISM: Artificial
<220> FEATURE:
<223> OTHER INFORMATION: synthetic primer

<400> SEQUENCE: 29
ataagagaat ccgtgagatc ccg                                        23

<210> SEQ ID NO 30
<211> LENGTH: 23
<212> TYPE: DNA
<213> ORGANISM: Artificial
<220> FEATURE:
<223> OTHER INFORMATION: synthetic primer

<400> SEQUENCE: 30
agatattcct gggacaactg gtg                                        23

<210> SEQ ID NO 31
<211> LENGTH: 22
<212> TYPE: DNA
<213> ORGANISM: Artificial
<220> FEATURE:
<223> OTHER INFORMATION: synthetic primer

<400> SEQUENCE: 31
tcatcgatct tgtgtaggtc tg                                         22

<210> SEQ ID NO 32
<211> LENGTH: 20
<212> TYPE: DNA
<213> ORGANISM: Artificial
<220> FEATURE:
<223> OTHER INFORMATION: synthetic primer

<400> SEQUENCE: 32
cgaaggaagc accagttgtc                                            20

<210> SEQ ID NO 33
<211> LENGTH: 24
<212> TYPE: DNA
<213> ORGANISM: Artificial
<220> FEATURE:
<223> OTHER INFORMATION: synthetic primer
```

-continued

```
<400> SEQUENCE: 33
aaaaactcat cagcatcatc attc                                              24
```

FLOWERING INDUCTION

The present invention relates to nucleic acid fragments encoding amino acid sequences for proteins involved in the control of flowering in plants, and the use thereof for the modification of flowering in plants.

Genetic pathways that control flowering time in the model plant *Arabidopsis thaliana* have been extensively studied recently, and great progress in identification of genes that control key steps in these pathways has been made (see[1-4] for a review). For example, it has been found that increased expression of the flowering locus T (FT) gene leads to accelerated floral development, and almost complete loss of a normal photoperiodic response[5-7]. It has also been shown that, when combined with the increased expression of the meristem identity gene LEAFY, FT over-expression leads to essential elimination of the vegetative stage in the plant development, so that the emerging seedlings do not produce any non-floral apical organs other than the first two leaves[5,6]. Combined over-expression of AP1 and LEAFY genes to facilitate transition to floral development has also been described[8,9]

Data to support the *arabidopsis* model of the genetic control of flowering time as applicable to other plant species was sparse until fairly recently. However, significant advances in the rice heading date QTL mapping[10] and identification of the genes underlying natural variation revealed the same genetic pathway, at least for the photoperiodic control of flowering[11-13], despite the fact that rice has the short day photoperiod as opposed to the long day one of *arabidopsis*. Increased expression of the putative rice ortholog of FT called Hd3a seems to correlate with transition to flowering[14].

While nucleic acid sequences encoding some of the enzymes involved in the control of flowering have been isolated for certain species of plants, there remains a need for materials useful in the modification of flowering in a wide range of plants, and for methods for their use.

Accordingly there is a need for a system of accelerating flowering in plants. In particular there is a need for such a system in forage plants.

It is an object of the present invention to overcome, or at least alleviate, one or more of these needs in light of the prior art.

In one aspect, the present invention provides substantially purified or isolated nucleic acids encoding amino acid sequences of FLOWERING LOCUS T (FT) enzymes, and functionally active fragments and variants thereof.

The present invention also provides substantially purified or isolated nucleic acid fragments encoding amino acid sequences for a class of polypeptides, which are related to FT. Such polypeptides are referred to herein as FT-like. The genes which encode these polypeptides are expressed in a similar manner to FT. The invention also encompasses functionally active fragments and variants of nucleic acids encoding such polypeptides.

As used herein the term FT-like relates to polypeptides that are produced in the plant in substantially the same organs and at substantially the same developmental stages as FT.

The nucleic acid fragments are obtained from ryegrass (*Lolium*) or fescue (*Festuca*) species. These species may be of any suitable type, including Italian or annual ryegrass, perennial ryegrass, tall fescue, meadow fescue and red fescue. Preferably the species is a ryegrass, more preferably perennial ryegrass (*L. perenne*).

Nucleic acids according to the invention may be full-length genes or part thereof, and are also referred to as "nucleic acid fragments" and "nucleotide sequences" on this specification.

The nucleic acid fragment may be of any suitable type and includes DNA (such as cDNA or genomic DNA) and RNA (such as mRNA) that is single- or double-stranded, optionally containing synthetic, non-natural or altered nucleotide bases, and combinations thereof.

The term "isolated" means that the material is removed from its original environment (eg. the natural environment if it is naturally occurring). For example, a naturally occurring nucleic acid fragment or polypeptide present in a living plant is not isolated, but the same nucleic acid fragment or polypeptide separated from some or all of the coexisting materials in the natural system, is isolated. Such an isolated nucleic acid fragment could be part of a vector and/or such nucleic acid fragments could be part of a composition, and still be isolated in that such a vector or composition is not part of its natural environment.

By "functionally active" in respect of a nucleotide sequence is meant that the fragment or variant (such as an analogue, derivative or mutant) is capable of modifying flowering in a plant. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence, more preferably at least approximately 90% identity, most preferably at least approximately 95% identity. Such functionally active variants and fragments include, for example, those having nucleic acid changes which result in conservative amino acid substitutions of one or more residues in the corresponding amino acid sequence. Preferably the fragment has a size of at least 30 nucleotides, more preferably at least 45 nucleotides, most preferably at least 60 nucleotides.

By "functionally active" in the context of a polypeptide is meant that the fragment or variant has one or more of the biological properties of the FT protein. Additions, deletions, substitutions and derivatizations of one or more of the amino acids are contemplated so long as the modifications do not result in loss of functional activity of the fragment or variant. Preferably the functionally active fragment or variant has at least approximately 60% identity to the relevant part of the above mentioned sequence, more preferably at least approximately 80% identity, most preferably at least approximately 90% identity. Such functionally active variants and fragments include, for example, those having conservative amino acid substitutions of one or more residues in the corresponding amino acid sequence. Preferably the fragment has a size of at least 10 amino acids, more preferably at least 15 amino acids, most preferably at least 20 amino acids.

By "operatively linked" is meant that said regulatory element is capable of causing expression of said nucleic acid in a plant cell and said terminator is capable of terminating expression of said nucleic acid in a plant cell. Preferably, said regulatory element is upstream of said nucleic acid and said terminator is downstream of said nucleic acid.

By "an effective amount" is meant an amount sufficient to result in an identifiable phenotypic trait in said plant, or a plant, plant seed or other plant part derived therefrom. Such amounts can be readily determined by an appropriately skilled person, taking into account the type of plant, the route of administration and other relevant factors. Such a person will readily be able to determine a suitable amount and method of administration. See, for example, Maniatis et al, Molecular Cloning: A Laboratory Manual, Cold Spring Harbor Laboratory, Cold Spring Harbor, the entire disclosure of which is incorporated herein by reference.

It will also be understood that the term "comprises" (or its grammatical variants) as used in this specification is equivalent to the term "includes" and should not be taken as excluding the presence of other elements or features.

Reference to any prior art in the specification is not, and should not be taken as, an acknowledgment or any form of suggestion that this prior art forms part of the common general knowledge in Australia or any other jurisdiction.

In a preferred embodiment of this aspect of the invention, the substantially purified or isolated nucleic acid fragment encoding a FT protein includes a nucleotide sequence selected from the group consisting of (a) sequence shown in FIG. 1 hereto (Sequence ID No. 1); (b) complements of the sequence recited in (a); (c) sequences antisense to the sequences recited in (a) and (b); (d) functionally active fragments and variants of the sequences recited in (a), (b) and (c); and (e) RNA sequences corresponding to the sequences recited in (a), (b), (c) and (d).

The nucleic acid fragments of the present invention may be used to isolate cDNAs and genes encoding homologous proteins from the same or other plant species.

Additionally, genes encoding other proteins involved in the control of flowering, either as cDNAs or genomic DNAs, may be isolated directly by using all or a portion of the nucleic acid fragments of the present invention as hybridisation probes to screen libraries from the desired plant employing the methodology known to those skilled in the art. Specific oligonucleotide probes based upon the nucleic acid sequences of the present invention can be designed and synthesized by methods known in the art. Moreover, the entire sequences can be used directly to synthesize DNA probes by methods known to the skilled artisan such as random primer DNA labelling, nick translation, or end-labelling techniques, or RNA probes using available in vitro transcription systems. In addition, specific primers can be designed and used to amplify a part or all of the sequences of the present invention. The resulting amplification products can be labelled directly during amplification reactions or labelled after amplification reactions, and used as probes to isolate full length cDNA or genomic fragments under conditions of appropriate stringency.

In addition, two short segments of the nucleic acid fragments of the present invention may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the nucleic acid fragments of the present invention, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, those skilled in the art can follow the RACE protocol[15] (the entire disclosure of which is incorporated herein by reference) to generate cDNAs by using PCR to amplify copies of the region between a single point in the transcript and the 3' or 5' end. Using commercially available 3' RACE and 5' RACE systems (BRL), specific 3' or 5' cDNA fragments can be isolated[16,17]. Products generated by the 3' and 5' RACE procedures can be combined to generate full-length cDNAs.

In a second aspect of the present invention there is provided a substantially purified or isolated FT polypeptide or FT-like polypeptide from a ryegrass (*Lolium*) or fescue (*Festuca*) species, or a functionally active fragment or variant thereof.

The ryegrass (*Lolium*) or fescue (*Festuca*) species may be of any suitable type, including Italian or annual ryegrass, perennial ryegrass, tall fescue, meadow fescue and red fescue. Preferably the species is a ryegrass, more preferably perennial ryegrass (*L. perenne*).

In a preferred embodiment of this aspect of the invention, there is provided a substantially purified or isolated FT polypeptide including an amino acid sequence translated from nucleotide sequence shown in FIG. 1 hereto; and functionally active fragments and variants thereof.

In a further embodiment of this aspect of the invention, there is provided a polypeptide recombinantly produced from a nucleic acid according to the present invention. Techniques for recombinantly producing polypeptides are known to those skilled in the art.

Availability of the nucleotide sequences of the present invention and deduced amino acid sequences facilitates immunological screening of cDNA expression libraries. Synthetic peptides representing portions of the instant amino acid sequences may be synthesized. These peptides can be used to immunise animals to produce polyclonal or monoclonal antibodies with specificity for peptides and/or proteins comprising the amino acid sequences. These antibodies can be then used to screen cDNA expression libraries to isolate full-length cDNA clones of interest.

A genotype is the genetic constitution of an individual or group. Variations in genotype are essential in commercial breeding programs, in determining parentage, in diagnostics and fingerprinting, and the like. Genotypes can be readily described in terms of genetic markers. A genetic marker identifies a specific region or locus in the genome. The more genetic markers, the finer defined is the genotype. A genetic marker becomes particularly useful when it is allelic between organisms because it then may serve to unambiguously identify an individual. Furthermore, a genetic marker becomes particularly useful when it is based on nucleic acid sequence information that can unambiguously establish a genotype of an individual and when the function encoded by such nucleic acid Is known and is associated with a specific trait. Such nucleic acids and/or nucleotide sequence information including single nucleotide polymorphisms (SNPs), variations in single nucleotides between allelic forms of such nucleotide sequence, can be used as perfect markers or candidate genes for the given trait.

In a further aspect of the present invention there is provided a method of isolating a nucleic acid of the present invention including a single nucleotide polymorphism (SNP), said method including sequencing nucleic acid fragments from a nucleic acid library.

The nucleic acid library may be of any suitable type and is preferably a cDNA library. The nucleic acid fragments may be isolated from recombinant plasmids or may be amplified, for example using polymerase chain reaction. The sequencing may be performed by techniques known to those skilled in the art.

In a further aspect of the present invention, there is provided use of nucleic acids of the present invention including SNP's, and/or nucleotide sequence information thereof, as molecular genetic markers.

In a further aspect of the present invention there is provided use of a nucleic acid according to the present invention, and/or nucleotide sequence information thereof, as a molecular genetic marker. More particularly, nucleic acids according to the present invention and/or nucleotide sequence information thereof may be used as a molecular genetic marker for quantitative trait loci (QTL) tagging, QTL mapping, DNA fingerprinting and in marker assisted selection, particularly in ryegrasses and fescues. Even more particularly, nucleic acids according to the present invention and/or nucleotide sequence information thereof may be used as molecular genetic markers in forage and turf grass improvement, e.g. tagging QTLs for herbage quality traits, dry matter digestibility, mechanical stress tolerance, disease resistance, insect pest resistance, plant stature, leaf and stem colour. Even more particularly, sequence information revealing SNPs in allelic variants of the nucleic acids of the present invention and/or nucleotide sequence information thereof may be used as molecular genetic markers for QTL tagging and mapping and in marker assisted selection, particularly in ryegrasses and fescues.

In a still further aspect of the present invention there is provided a construct including a nucleic acid according to the present invention. The construct may be a vector. In a preferred embodiment of this aspect of the invention, the vector may include a regulatory element such as a promoter, a nucleic acid according to the present invention and a terminator; said regulatory element, nucleic acid and terminator being operatively linked.

The vector may be of any suitable type and may be viral or non-viral. The vector may be an expression vector. Such vectors include chromosomal, non-chromosomal and synthetic nucleic acid sequences, eg. derivatives of plant viruses; bacterial plasmids; derivatives of the Ti plasmid from *Agrobacterium tumefaciens*, derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable, or integrative or viable in the plant cell.

The regulatory element and terminator may be of any suitable type and may be endogenous to the target plant cell or may be exogenous, provided that they are functional in the target plant cell.

In another embodiment, the construct or vector may include more than one nucleic acid. The nucleic acids within the same construct or vector may have identical or differing sequences. In one preferred embodiment, the construct or vector has at least two nucleic acids encoding more than one protein involved in the regulation of flowering.

In another preferred embodiment, the construct or vector includes a nucleic acid or nucleic acid fragment according to the present invention and a meristem identity gene. The meristem identity gene may be selected from a group consisting of LEAFY (LFY), APETALA1 (AP1), CONSTANS (CO), FLORICAULA (FLO), SQUAMOSA (SQUA), FLOWERING LOCUS CA (FCA) and combinations thereof.

Preferably one of the regulatory elements is a promoter. A variety of promoters which may be employed in the vectors of the present invention are well known to those skilled in the art. Factors influencing the choice of promoter include the desired tissue specificity of the vector, and whether constitutive or inducible expression is desired and the nature of the plant cell to be transformed (eg. monocotyledon or dicotyledon). Particularly suitable constitutive promoters include the Cauliflower Mosaic Virus 35S (CaMV 35S) promoter, the maize Ubiquitin promoter, and the rice Actin promoter.

In one preferred embodiment, the promoter is inducible, to allow for artificial induction of gene expression. It will be appreciated by a person skilled in the art that a variety of known inducible expression systems may be used.

For example, systems utilizing the glucocorticoid receptor (GR) domain for regulation using dexmethasone (DEX) have been used successfully in plants[18], as well as ones utilizing the bacterial DNA recognition sequences in a combination called LhG4-GR[19], or parts of the alcohol-inducible operon AlcR of aspergillus [20,21]. It is also possible to isolate plant promoters responding directly to certain chemical treatment like herbicide safeners[22].

A variety of terminators which may be employed in the vectors of the present invention are also well known to those skilled in the art. It may be from the same gene as the promoter sequence or a different gene. Particularly suitable terminators are polyadenylation signals, such as the CaMV 35S polyA and other terminators from the nopaline synthase (nos) and the octopine synthase (ocs) genes.

The vector, in addition to at least one regulatory element, the nucleic acid of the present invention and the terminator, may include further elements necessary for expression of the nucleic acid, in different combinations, for example vector backbone, origin of replication (ori), multiple cloning sites, spacer sequences, enhancers, introns (such as the maize Ubiquitin Ubi intron), antibiotic resistance genes and other selectable marker genes [such as the neomycin phosphotransferase (npt2) gene, the hygromycin phosphotransferase (hph) gene, the phosphinothricin acetyltransferase (bar or pat) gene), and reporter genes (such as beta-glucuronidase (GUS) gene (gusA)]. The vector may also contain a ribosome binding site for translation initiation. The vector may also include appropriate sequences for amplifying expression.

As an alternative to use of a selectable marker gene to provide a phenotypic trait for selection of transformed host cells, the presence of the construct or vector in transformed cells may be determined by other techniques well known in the art, such as PCR (polymerase chain reaction), Southern blot hybridisation analysis, histochemical GUS assays, northern and Western blot hybridisation analyses.

Those skilled in the art will appreciate that the various components of the construct or vector are operatively linked, so as to result in expression of said nucleic acid. Techniques for operatively linking the components of the construct or vector of the present invention are well known to those skilled in the art. Such techniques include the use of linkers, such as synthetic linkers, for example including one or more restriction enzyme sites.

The constructs and vectors of the present invention may be incorporated into a variety of plants, including monocotyledons (such as grasses from the genera *Lolium, Festuca, Paspalum, Pennisetum, Panicum* and other forage and turfgrasses, corn, rice, sugarcane, oat, wheat and barley, dicotyledons, such as *arabidopsis*, tobacco, soybean, canola, cotton, potato, chickpea, medics, white clover, red clover, subterranean clover, alfalfa, eucalyptus, poplar, hybrid aspen, and gymnosperms (pine tree). In a preferred embodiment, the constructs and vectors are used to transform monocotyledons, preferably grass species such as ryegrasses (*Lolium* species) and fescues (*Festuca* species), even more preferably a ryegrass, most preferably perennial ryegrass, including forage- and turf-type cultivars.

Techniques for incorporating the constructs and vectors of the present invention into plant cells (for example by transduction, transfection or transformation) are well known to those skilled in the art. Such techniques include *Agrobacterium* mediated introduction, electroporation to tissues, cells and protoplasts, protoplast fusion, injection into reproductive organs, injection into immature embryos and high velocity projectile introduction to cells, tissues, calli, immature and mature embryos. The choice of technique will depend largely on the type of plant to be transformed.

Cells incorporating the constructs and vectors of the present invention may be selected, as described above, and then cultured in an appropriate medium to regenerate transformed plants, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

In a further aspect of the present invention there is provided a plant cell, plant, plant seed or other plant part, including, e.g. transformed with, a construct or vector of the present invention.

The plant cell, plant, plant seed or other plant part may be from any suitable species, including *monocotyledons, dicotyledons* and *gymnosperms*. In a preferred embodiment the plant cell, plant, plant seed or other plant part is from a monocotyledon, preferably a grass species, more preferably a ryegrass (*Lolium* species) or fescue (*Festuca* species), even more preferably a ryegrass, most preferably perennial ryegrass, including both forage- and turf-type cultivars.

The present invention also provides a plant, plant seed or other plant part derived from a plant cell of the present invention. The present invention also provides a plant, plant seed or other plant part derived from a plant of the present invention. Such a transgenic plant may include an inducible system for controlling the expression of a nucleic acid according to the present invention. To make the expression controllable, the genes are expressed in a transgenic plant from a heterologous inducible system described above. Appropriate transgenic plants will then reliably flower in response to the artificial inductive treatment i.e. dexmethasone application, rather than due to the natural signals. The scope of invention is not limited to the dexmethasone inducible system, any other existing or new methodology that allows controlled expression of the genes at the same time can be used in the similar way. The invention covers the inducible manipulation of expression to the perennial ryegrass FT and other flowering genes to manipulate flowering characteristics in perennial ryegrass.

In a further aspect of the present invention there is provided a method of modifying flowering in a plant, said method including introducing into said plant an effective amount of a nucleic acid, construct and/or vector according to the present invention. Preferably the method includes inhibiting flowering in said plant.

In a preferred embodiment, the method results in the induction of more than one gene encoding a protein involved in the regulation of flowering. In a particularly preferred embodiment, floral development is activated or accelerated in the plant.

Using the methods and materials of the present invention, flowering may be accelerated or delayed. It may be accelerated, for example, by incorporating additional copies of a sense nucleic acid of the present invention. It may be delayed, for example, by incorporating an antisense nucleic acid or dsRNA or small interfering RNA (siRNA) derived from the nucleotide sequences of the present invention. In addition, the number of copies of genes encoding for different proteins involved in control of flowering may be manipulated to modify the flowering of a plant.

In a further aspect of the present invention there is provided a preparation for transforming a plant comprising at least one nucleic acid according to the present invention. The preparation may contain vectors or other constructs to facilitate administration to and/or transformation of the plant with the nucleic acid.

The principle of inducible flowering described here can be applied to forage grasses like ryegrass to better control pasture production cycle, and to improve persistence by allowing a more controlled heading. Its application however is not limited to forage grasses, and such inducible system can be applied to any agricultural crop to facilitate more controlled production, and reduce dependence of yields on weather.

The present invention will now be more fully described with reference to the accompanying Examples and drawings. It should be understood, however, that the description following is illustrative only and should not be taken in any way as a restriction on the generality of the invention described above.

In the Figures:

FIG. 1 shows the sequence of the RgFT3 cDNA (Sequence ID No. 1).

FIG. 4 shows the principle behind the inducible expression system.

Figure 6:
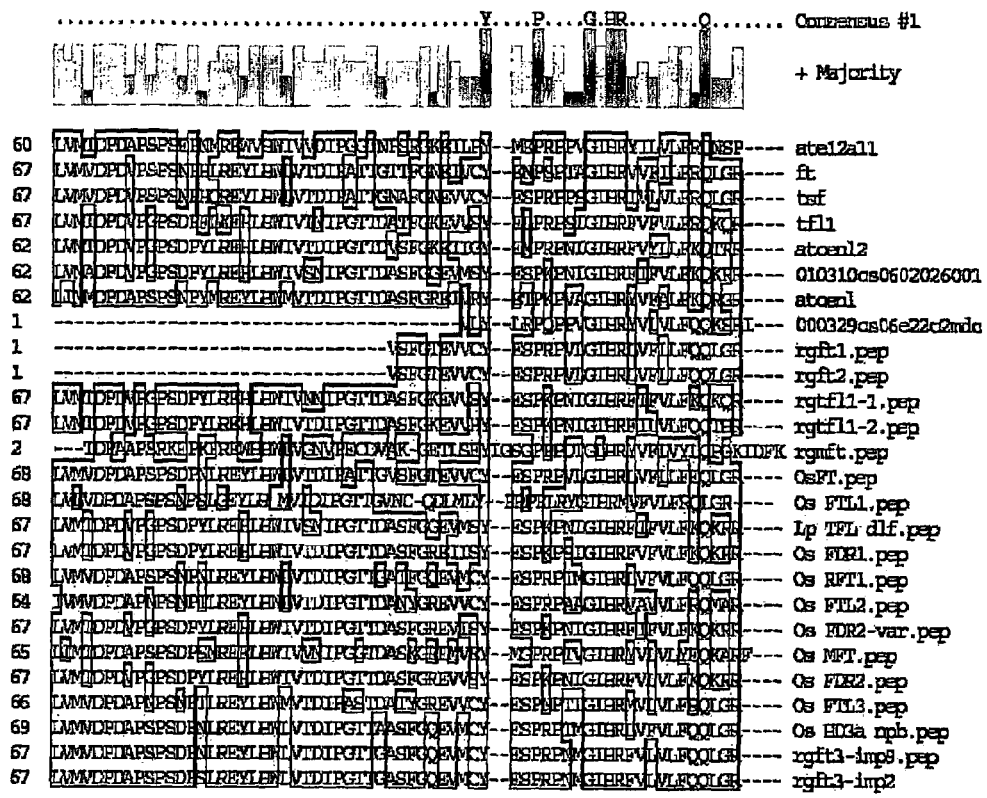
Figure 6:
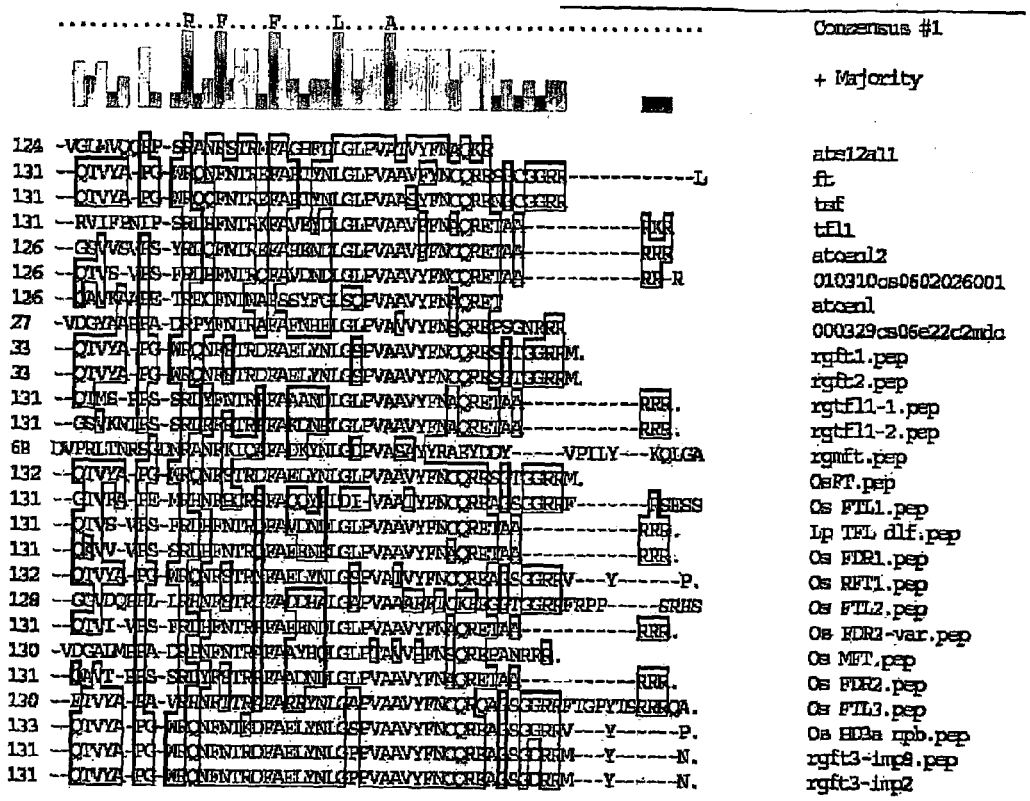

FIG. 6 shows the alignment between FT genes from various species, as follows: ate12a11 is SEQ ID NO: 2 from *Arabidopsis thaliana*, ft is SEQ ID NO: 3 from *Arabidopsis thaliana*, tsf is SEQ ID NO: 4 from *Arabidopsis thaliana*, tfl1 is SEQ ID NO: 5 from *Arabidopsis thaliana*, atcenl1 is SEQ ID NO: 6 from *Arabidopsis thaliana*, 010310cs0602026001 is SEQ ID NO: 7 from *Lolium perenne*, atcenl is SEQ ID NO: 8 from *Arabidopsis thaliana*, 000329cs06e22c2rdc is SEQ ID NO: 9 from *Lolium perenne*, rgft1.pep is SEQ ID NO: 10 from *Lolium perenne*, rgft2.pep is SEQ ID NO: 11 from *Lolium perenne*, rgtfl1-1.pep is SEQ ID NO: 12 from *Lolium perenne*, rgtfl1-1.pep is SEQ ID NO: 13 from *Lolium perenne*, rgmft.pep is SEQ ID NO: 14 from *Lolium perenne*, OsFT.pep is SEQ ID NO: 15 *Oryza sativa*, Os FLT1.pep is SEQ ID NO: 16 from *Oryza sativa*, Lp TFL dlf.pep is SEQ ID NO: 17 from *Lolium perenne*, Os FDR1.pep is SEQ ID NO: 18 from *Oryza sativa*, Os RFT1.pep is SEQ ID NO: 19 from *Oryza sativa*, Os FTL2.pep is SEQ ID NO: 20 from *Oryza sativa*, Os FDR2-var.pep is SEQ ID NO: 21 from *Oryza sativa*, Os MFT.pep is SEQ ID NO: 22 from *Oryza sativa*, Os FDR2.pep is SEQ ID NO: 23 from *Oryza sativa*, Os FTL2.pep is SEQ ID NO: 24 from *Oryza sativa*, Os HD3a.npb.pep is SEQ ID NO: 25 from *Oryza sativa*, rgft-imp8.pep is SEQ ID NO: 26 from *Lolium perenne*, and rgft3-imp2 is SEQ ID NO: 27 from *Lolium perenne*.

Figure 7:
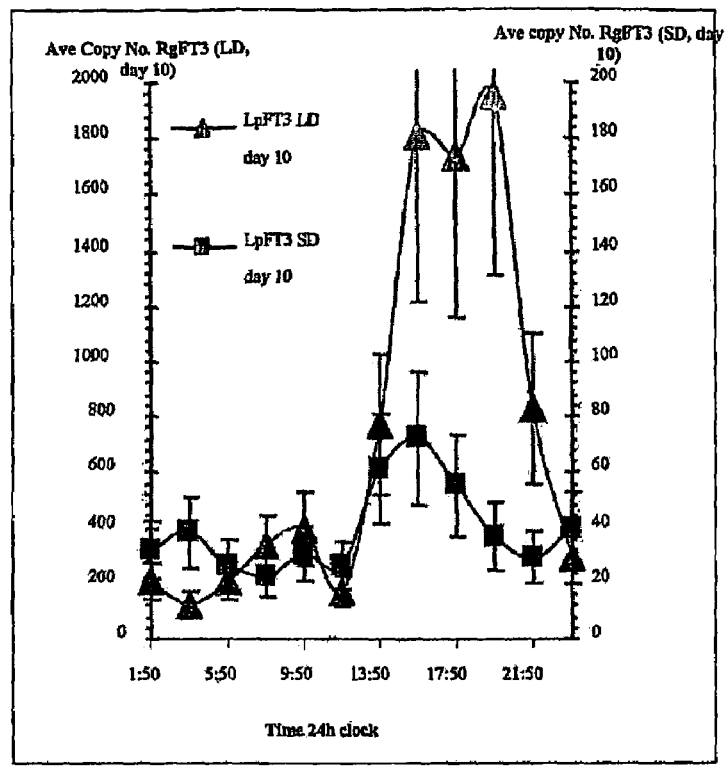
Figure 8:
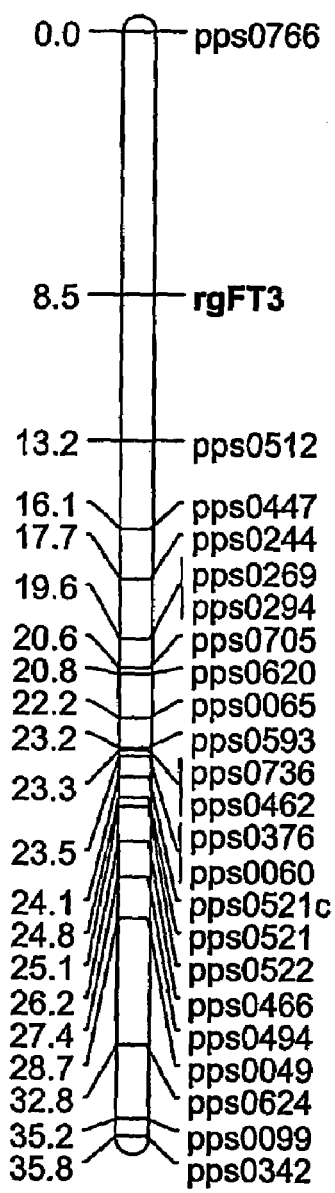

FIG. 7 shows diurnal change in mRNA expression levels of the RgFT3 gene over 24-hr period in short and long day conditions FIG. 8 shows a genetic linkage map of perennial ryegrass linkage group LG7 showing the map position of the RgFT3 gene. Marker locus names are indicated on the right side of the bar, with centimorgan (cM) distances on the left. The rgFT3 SNP marker is indicated in bold. The remaining loci, prefixed 'pps', are EST-SSR loci.

Figure 9:
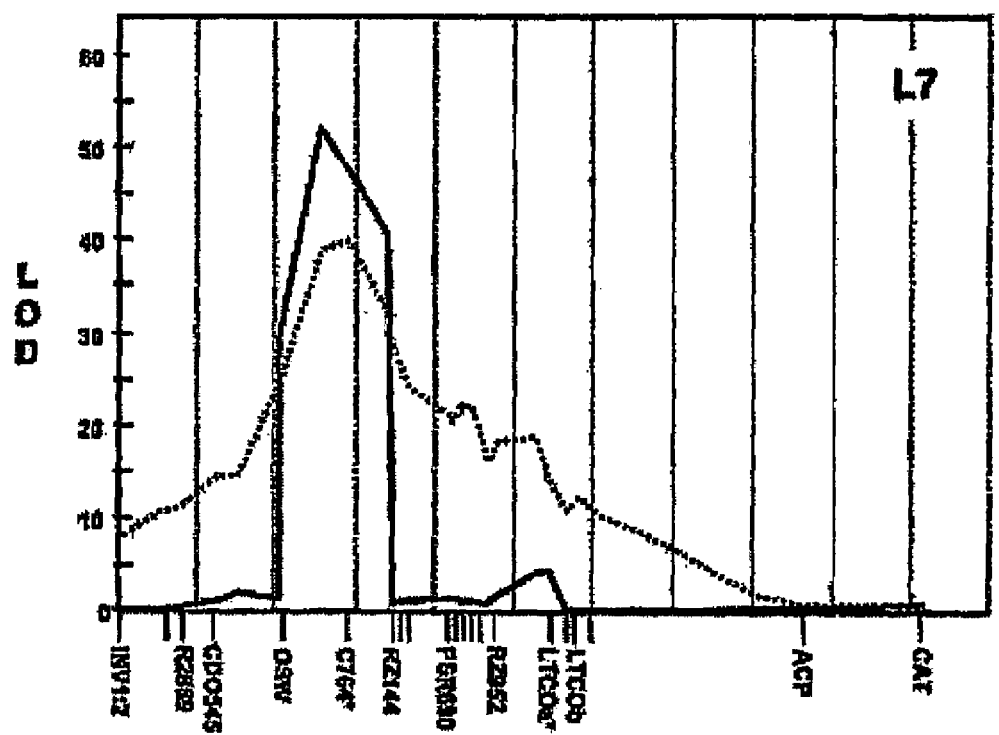

FIG. 9 is adopted from a publication, and illustrates a major heading date QTL mapped to the RgFT3 gene region (from Armstead, I.P. et al. (2004) Synteny between a major heading-date QTL in perennial ryegrass (*Lolium perenne* L.) and the Hd3 heading-date locus in rice. *Theor Appl Genet* 108, 822-828), see the cited. publication for details.

Figure 10:
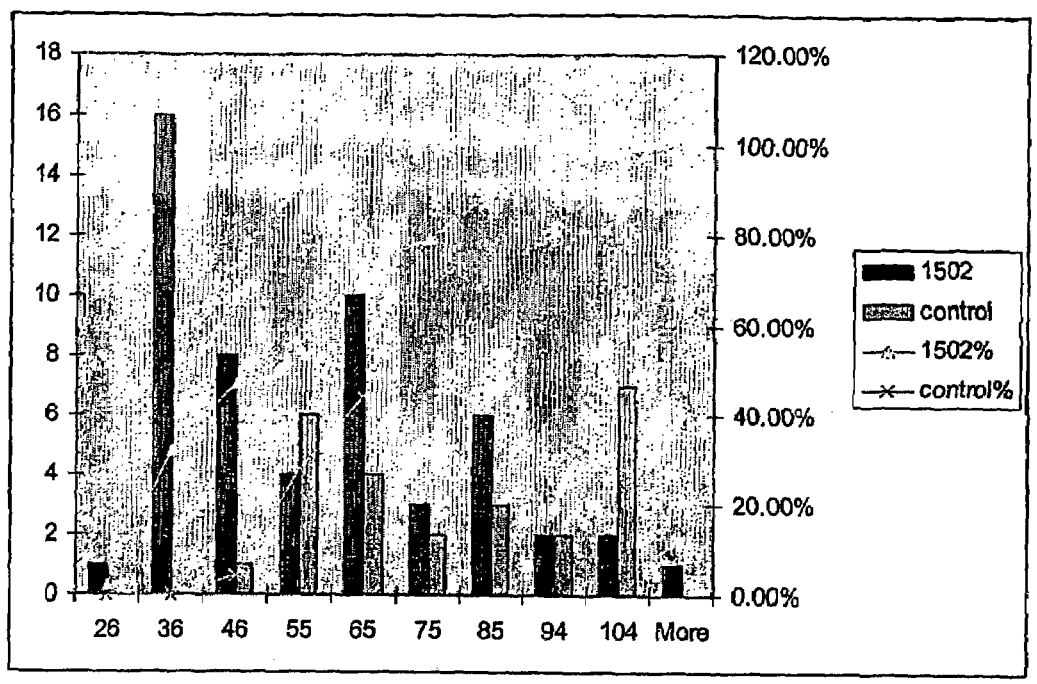

FIG. 10 shows distribution of heading dates in transgenic ryegrass plants overexpressing the FT gene. Heading data (days) for two populations of ryegrass are presented as frequency distribution and cumulative percentages. '1502' is a back-cross population derived from crossing the 1502 transgenic plant to the Progrow untransformed parent, 'control' are the Progrow plants grown in parallel.

Figure 11:

FIG. 11 is a photograph of such transgenic plant alongside with a control plant. The early flowering plant from the 1502 back-cross segregating population is compared to the non-transformed parent, grown side-by-side.

Figure 12:

FIG. 12 shows the effect inducing expression of the *arabidopsis* gene in *arabidopsis*. *Arabidopsis* plants containing the pHTOP::FT inducible construct were sprayed with 30 mM DEX (right), or covered with plastic to prevent spraying (left). Panel on top shows the plants just after spraying, panel below shows plants 6 days later when inflorescences have emerged on the sprayed plants.

EXAMPLES

Gene Isolation

A *Lolium perenne* gene called RgFT3 was isolated, which was considered to be an ortholog of the *arabidopsis* FT gene. The gene was isolated using conserved sequence elements by using degenerate primers. In addition to RgFT3, we also isolated partial sequence of the other two FT-like genes of ryegrass, called RgFT1 and 2, and 2 members of the TFL-like subfamily RgTFL1 and 2, that share significant sequence similarity with FT, but perform the opposite function of floral repression in *arabidopsis*[23-25]. Together with the previously published gene, [26]these comprise 7 genes of similar sequence that may be involved in regulation of flowering, as compared with 6 genes in *arabidopsis*, and 9 genes described in rice. The sequence of RgFT3 is shown in FIG. 1.

Sequence Comparisons

Figure 2:
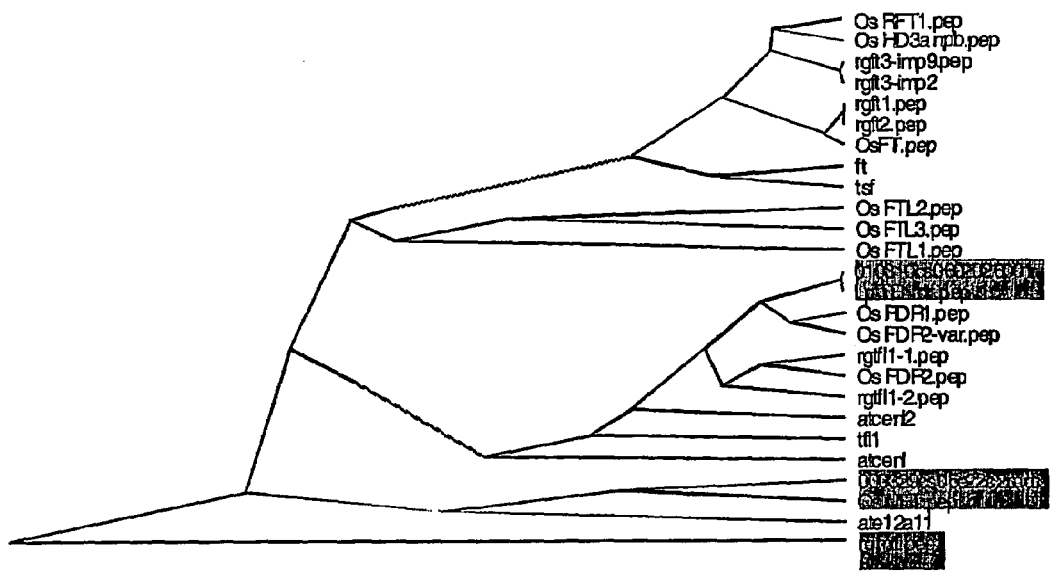
FIG. 2 shows a comparison of translated protein sequences for RgFT3 and genes from other species.

Alignment of translated protein sequences for these and other genes is shown in the appendix 1, the corresponding tree is shown in FIG. 2.

The RgFT3 sequence clusters with the other FT-like sequences in this alignment, and is highly similar to the rice Hd3a gene sequence that was shown to affect flowering time by QTL analysis[11], and to be regulated by the circadian clock and other genetic components of the photoperiodic perception pathway[14].

The RgFT3 gene therefore can be used to accelerate transition to flowering if the gene is ectopically expressed, or to suppress normal transition if its expression is reduced via targeted mutagenesis or RNA interference.

(a) Expression Analysis of the RgFT3 Gene

Methods:

Ryegrass plants were grown outside and subjected to cold over the winter to achieve natural vernalization. They were then transferred to a glass house, and grown either in natural short day (SD) conditions (<11 hrs daylight), or with supplementary light to create artificial long day (LD) conditions (18 hr day). End of day in both conditions was at ~18:00. Plant samples were harvested as entire above-ground tillers 10 days after the long day treatment started, samples were taken every 2 hrs for 24 hours from both LD and SD treated plants.

Total RNA was extracted from samples using the Trizol protocol as follows:

Extraction of RNA from 1 g (nett) of *L. perenne* plant tissue using the Trizol® Reagent (Invitrogen)

Plant Tissue Pre-homogenisation Treatment

Remove relevant bags of plant tissue from −80° C. freezer. Keep frozen in liquid $N_2$ or on dry ice until ready for treatment. Prechill coffee grinder by processing two dry ice pellets (7 g pellets).

NB: In between samples, wipe out the coffee grinder with 75% ethanol soaked kim wipes and repeat prechill step Weigh bag of tissue (approx 7-10 g). Empty contents into coffee grinder and blend until tissue is the consistency of salt granules (no larger). Pour coarsely ground tissue into a fresh prechilled bag (the old ones tend to get holes when handled) and keep frozen until required for next stage. Reweigh just before taking sample for fine grinding (allowing for difference in bag weight). After a few measurements we assumed that the dry ice component of the sample was approximately 10% of sample weight.

Homogenisation

Remove 1.1-1.2 g of coarsely ground tissue (taking into account the increase of weight due to dry ice contribution) and ⊛homogenise further in a prechilled mortar containing liquid $N_2$ until consistency of icing sugar. Add powder to 10 ml of Trizol® in mortar (room temperature) and homogenise further as quickly as possible. Pour soup into 14 ml disposable falcon tube. ⊛Incubate samples at least 5 min at RT with gentle inversion.

Phase Separation

Add 2 ml chloroform per sample. Cap and mix vigorously 15 s by hand. Incubate RT 2-3 min. Spin in swinging bucket rotor at 3200×g for 30 min⊛. Remove 4 ml to fresh tube (with modified cap*). There will be ~1 ml aqueous phase left, purposely done to reduce/avoid DNA contamination.

RNA Precipitation

Add 5 ml Isopropanol⊛. Mix by inversion ~6 times. Incubate for 10 min at RT. Centrifuge at ≦12,000×g for 10 mins. Decant and discard supernatant.

RNA Wash

Add 10 ml 75% ethanol. Vortex and mix by inversion to wash lid. ⊛Centrifuge ≦7,500×g, 5 mins, 4° C. Decant and discard supernatant. To reduce drying time, centrifuge again to collect excess wash solution to bottom of the tube at ≦7,500×g, 2 mins, 4° C. Remove excess liquid with RNAse-free pipette tip and air-dry pellet approx 10-15 min.

RNA Resuspension

Add 0.8 ml of DEPC treated water. Gently resuspend pellet with pipette tip. Transfer liquid to eppendorf tube. An incubation at 55 C for 10 min may be required if resuspension difficult.

RNA Storage

Store samples labelled well at −80° C. with bulk sample ~700 ul and a 80 ul working aliquot.

Total RNA was converted to cDNA using standard protocols using 1-5 ug of RNA as measured by OD260.

Quantitative RT-PCR was performed in the BioRad iCycler instrument using standard protocols and SyberGreen as reporting dye Actin gene levels were assayed using oligonucleotides GTF037 (Seq ID. No. 28) 5'GCTGTTTTCCCTAGCATTGT-TGG3' and GTF038 (Seq ID No. 29) 5'ATAAGAGAATC-CGTGAGATCCCG3', and served as standards to normalize measurements of other genes.

RgFT3 mRNA levels were measured using oligonucleotides GIK033 (Seq ID No. 30) 5'AGATATTCCTGGGA-CAACTGGTG3' and GIK040 (Seq ID No. 31) 5'TCATC-GATCTTGTGTAGGTCTG3'

To create a copy number calibration curve for individual genes, standards were made up from corresponding PCR products, measuring their concentration using gel serial dilution methods and spectrophotometry. Standard copy numbers were varied from 1 to 10^8 with 10× increments.

Amplifications were performed in triplicates, error rates were estimated by adding the average variance between triplicate samples, and average error of the standard curve fit of the standards of both the gene of interest and of the actin standard.

Results

The mRNA levels of the RgFT3 gene change significantly over the 24-hour cycle, reaching maximum as dusk, with peak-to-trough ratio of ~3× in short days, and >6× in long days. The periodicity of expression suggests that the ryegrass gene is under the control of the circadian clock, as are its orthologues in other plant species.

In photo inductive conditions, the gene expression level increases at least 30-fold in 10 days of long day exposure.

Both the circadian expression, and up regulation in photo inductive conditions strongly support the role of the RgFT3 gene in mediating and controlling the photoperiodic floral response of ryegrass. Similar expression pattens have been published for all plant species where the FT gene orthologues were identified and analysed.

(b) Establishing Map Position of the RgFT3 Gene.

Methods:

Plant Material and DNA Isolation

The perennial ryegrass population used for the genetic mapping of the rgFT3 SNP (single nucleotide polymorphism) marker and SSR (simple sequence repeat) markers was an $F_1$ progeny set derived from a pair cross between the heterozygous parental genotypes A8830/1030 (from the cultivar 'Grasslands Samson') and A10622/2 (from the cultivar 'Grasslands Impact'). Ninety-four individual progeny from the population were used for genetic linkage analysis. Genomic DNA was extracted by the 1×CTAB method of Fulton et al. (1995).

EST-SSR and SNP Analysis

Genotypic data for 94 mapping population progeny was generated using 157 EST-SSRs and the rgFT3 SNP markers Imp366 and Imp9. EST-SSR PCR was conducted using the three primer protocol described by Schuelke (2000). An 8 μL reaction volume was used, containing 10 ng of genomic DNA, 2.5 mM magnesium chloride, 1×PCR buffer (Invitrogen, Carlsbad, Calif., USA), 0.05 mM of each dNTP, 0.0375 μM forward primer, 0.15 μM reverse primer, 0.15 μM of fluorescent-labelled M13 primer and 0.3 U of Platinum Taq DNA polymerase (Invitrogen). Fluorophores used were 6-FAM™, NED™, VIC™ and PET™ (Applied Biosystems, Foster City, Calif., USA). EST-SSR primers were synthesised and supplied by either Invitrogen or Integrated DNA Technologies (Coralville, Iowa, USA). PCR reactions were run in iCyclers (BioRad, Hercules, Calif., USA), employing the following profile: (1) 94° C. for 4:00 minutes, (2) 30 cycles of: 94° C. for 30 seconds, 55° C. for 30 seconds and 72° C. for 30 seconds, (3) 8 cycles of: 94° C. for 30 seconds, 53° C. for 30 seconds and 72° C. for 30 seconds, (4) 72° C. for 30 minutes.

PCR products were analysed on an ABI 3100 Genetic Analyser using a 22 cm capillary array with POP-7™ polymer (Applied Biosystems). Electropherograms were analysed using ABI Prism GeneScan (v 3.7, Applied Biosystems), and genotype data was scored using ABI Prism Genotyper (v 3.7, Applied Biosystems). The allelic status of the RgFT3 SNPs was determined by direct sequencing of amplification products produced with oligonucleotides GIK31 (SEQ ID No. 32) 5'CGAAGGAAGCACCAGTTGTC3' and GIK32 (SEQ ID No. 33) 5'AAAAACTCATCAGCATCATCATTC3'.

Genetic Linkage Analysis

The A8830/1030×A10622 population was analysed as a two-way pseudo-testcross (Grattapaglia and Sederoff 1994). Genetic linkage analysis was conducted using the CP module of JoinMap®3.0 software (www.kyazma.nl). Map distances in centimorgans (cM) were calculated using the Kosambi mapping function (Kosambi 1944). Genetic linkage maps were first established separately for A8830/1030 and A10622 using segregation data from EST-SSR and SNP markers that could be derived as dominant features. Polymorphic loci detected by the same EST-SSR primer pair at similar locations on the maps of both parents were used to identify and align homologous linkage groups in the two parental maps, and to check for consistency of recombination frequency between the parental genotypes. Parental datasets were then combined and a consensus genetic linkage map was constructed, using a maximum recombination frequency of 0.4 and minimum LOD threshold of 2.0.

Results

Genetic linkage analysis enabled the location of 126 EST-SSR loci and the rgFT3 SNP on a consensus map covering 354 cM across seven linkage groups (LG1-LG7). The rgFT3 SNP mapped to a location at position 8.5 cM on LG7 (FIG. 2). Hd3a is considered an orthologue of the RgFT3 gene, and was thus used to isolate the RgFT3 gene initially. After the provisional filing of this patent, Armstead et al have published the QTL analysis of the heading date data in their mapping population of *Lolium perenne*. One of the markers called they used was derived from the rice genomic sequence closely linked to the Hd3a rice locus, it is labelled as C764 in FIG. 3, and was mapped to the same linkage group 7 as in our map. Armstead et al discovered that in their population a major QTL controlling heading date is centred on the C764 marker, suggesting synteny in this region between rice and ryegrass. Our mapping data, together with this publication, very strongly support our assertion that the RgFT3 gene is a key component of the photoperiodic control of flowering.

The markers we have identified can be used in marker-assisted selection to manipulate flowering behaviour of ryegrass.

REFERENCES

Fulton T M, Chunwongse J, Tanksley S D (1995) Microprep protocol for extraction of DNA from tomato and other herbaceous plants. Plant Mol Biol Rep 13: 207-209

Grattapaglia D, Sederoff R (1994) Genetic linkage maps of *Eucalyptus grandis* and *Eucalyptus urophylla* using a pseudo-testcross: mapping strategy and RAPD markers. Genetics 137:1121-1137

Kosambi D D (1944) The estimation of map distances from recombination values. Ann Eugen 12:172-175

Schuelke M (2000) An economic method for the fluorescent labeling of PCR fragments. Nat Biotechnol 18: 233-234

Armstead, I. P. et al. (2004) Synteny between a major heading-date QTL in perennial ryegrass (*Lolium perenne* L.) and the Hd3 heading-date locus in rice. *Theor Appl Genet* 108, 822-828

(c) Expression of the *arabidopsis* FT Gene in Transgenic Ryegrass Affects Heading Date Methods The construct SK1053 that enables overexpression the *arabidopsis* FT gene in transgenic plants under the constitutive CaMV35S promoter has been described elsewhere (Kardailsky, I. et al. (1999) Activation Tagging of the Floral Inducer FT. Science 286 (5446), 1962-1965; U.S. Pat. No. 6,225, 530).

Primary transgenic plants were obtained in the Progrow background derived from Italian ryegrass. Three lines displayed accelerated flowering when maintained in the glasshouse under natural light conditions without vernalization. Floral heads from clones of these plants were bagged together in pairs with different clones of the untransformed Progrow plants to enable crossing. Seed was harvested, and the back-cross generation plants were grown under natural long-day conditions in the glasshouse. Heading date was recorded when three spikes emerged above the flag leaf, days were counted from sowing.

Results

Three transgenic lines were obtained in the Progrow background that showed accelerated flowering when transferred to soil from the regeneration media. To confirm genetic nature of this acceleration, they were back-crossed to a different clonal material of the parental variety, and the T1 generation grown from seed and assayed for heading date.

Figure 5:
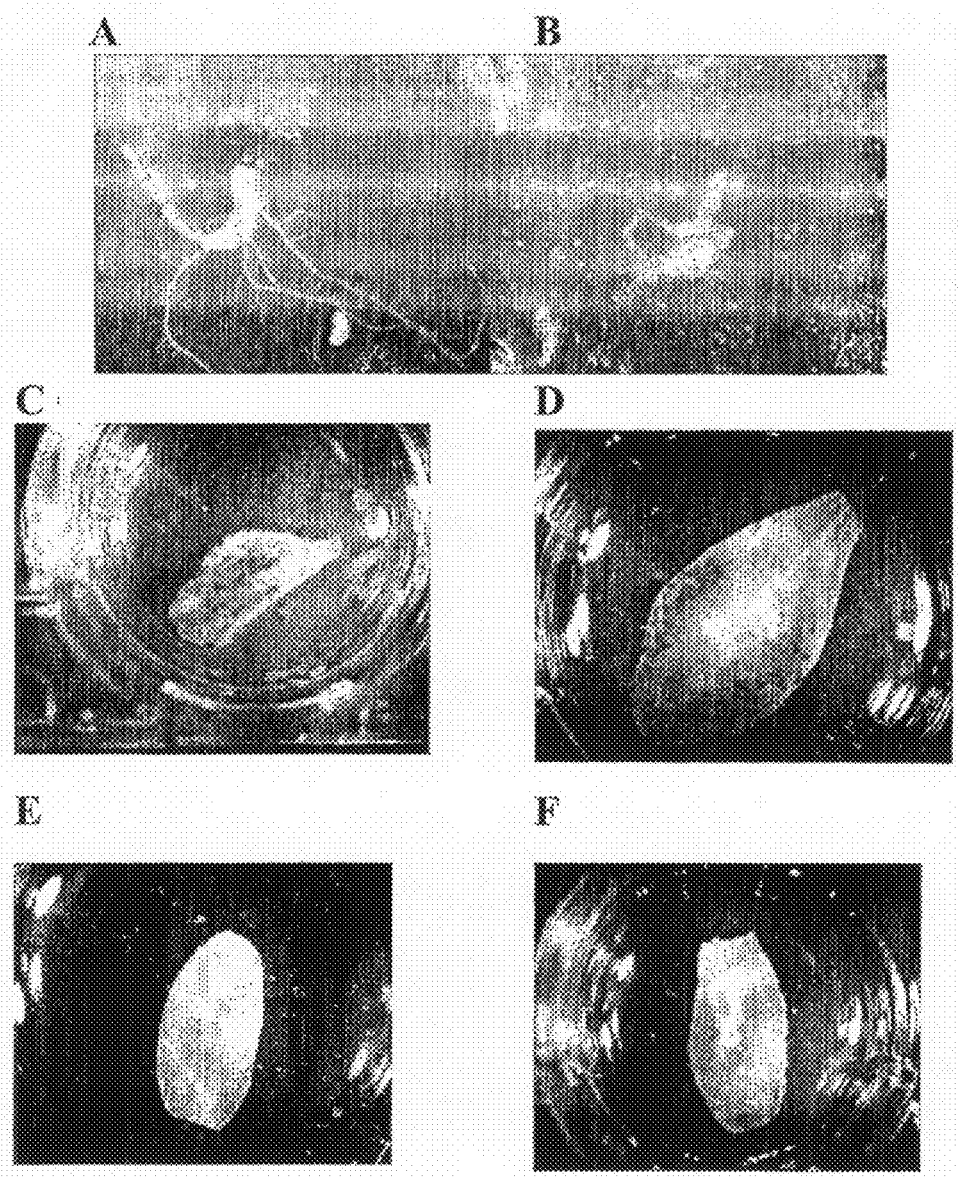
FIG. 5 shows the accelerated flowering and GUS staining of transgenic *Arabidopsis* plants containing pHTOP-FT. (A) A plant grown on a 30 µM MS-DEX plate; (B) No DEX control; (C) and (D) GUS staining of leaves from induced plants; (E) GUS staining of a leaf from a non-induced LhGr/pHtop-FT plant; GUS staining of a leaf from a Col wild type plant.

FIGS. 4 and 5 show comparison of heading dates between such backcross population derived from the primary line 1502 and the control untransformed plants grown side by side in the glasshouse. The 1502 population has a group of plants that flowered significantly earlier than others in the same population, and the control plants. This early group can be defined as plants with <55 days to heading, and they comprise ~50% of the total number of plants. Such distribution is characteristic of a single transgene in the heterozygous state in the 1502 line that now segregates in the back-cross population.

RgFT3 Gene Summary

We have isolated the ryegrass gene that is functionally equivalent to the *arabidopsis* FT gene, and called it the RgFT3. We used the rice Hd3a gene as a starting point in isolation, and conclude that the RgFT3 gene is FT orthologue based on the following criteria:

High level of nucleotide and protein sequence similarity

Circadian expression with maximum at dusk, and exponential increase in photoinductive conditions Genetic mapping places the gene in the region synthenic with rice Hd3a gene, and under a major heading date QTL in certain mapping populations Functional activity of the *arabidopsis* gene in ryegrass as evidenced by acceleration of heading in transgenic plants.

This evidence suggests strong conservation of the role of the FT-like genes, and the RgFT3 in particular, in controlling photoperiodic induction in ryegrass, and enables manipulation of heading date via alteration of the RgFT3 gene expression in ryegrass.

Inducible Expression of the FT Gene

Figure 3:
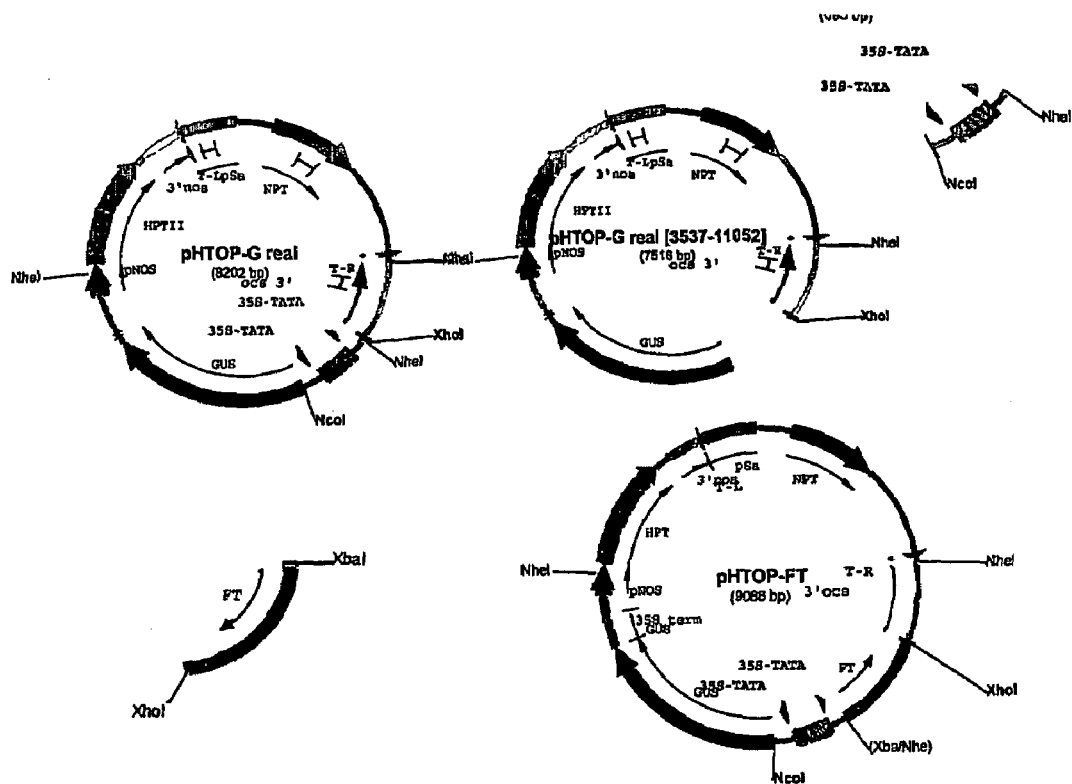
FIG. 3 shows a diagram of a construct containing *Arabidopsis* FT cDNA in an inducible pHTOP vector.

The *arabidopsis* FT cDNA was inserted into the pHTOP vector system to facilitate inducible expression of the gene using heterologous transcription factor system LhG4[19,27]. The cloning steps involved in the construction are shown in FIG. 3.

This inducible system allows for simultaneous expression of two genes from the same reporter construct. In the experiment described here the GUS gene was used as a second gene in addition to FT. The transactivator part and the principle of the induction is shown in FIG. 4.

We have shown that transgenic *arabidopsis* plants carrying both the pHTOP-FT construct and the LhG4-GR construct, and grown in the presence of the inducing steroid hormone DEX show both accelerated flowering, and GUS staining.

GUS was used as a reporter gene to demonstrate gene activity. The results of these experiments are shown in FIG. 5.

We have also measured the FT gene induction levels in the sprayed transgenic *arabidopsis* plants compared with the non-sprayed or non-transgenic controls in plants grown in short day conditions, the results are summarized in the table below:

| | treatment | fold gene induction |
|---|---|---|
| LhG4-mGR driver | 3 twice 30 µM | 1x |
| pHTOP::FT | 1 twice 30 nM | 1x |
| | 2 twice 1 µM | 20x |
| | 3 twice 30 µM | 120x |
| wild type | 0 no spray | 1x |
| | 3 twice 30 µM | 1x |

The methodology we used to measure the gene induction levels was essentially the same as described elsewhere in the patent, except that we used the *arabidopsis* gene-specific primers NIK13 5'CTACAACTGGAACAACCTTTG3' (SEQ ID NO: 34) and NIK14 5'ATCATCACCGTTCGTTACTC3' (SEQ ID NO: 35). We observed >100-fold induction in the cDNA level as assayed in real-time RT-PCR reaction in plants 3 days after they were treated with high (30 mM) level of the DEX inducer, and lesser induction with 1 mM spray of inducer.

This induction leads accelerated flowering as shown in the table below:

| genotype | line | 0 no spray | 1 twice 30 nM | 2 twice 1 µM | 3 twice 30 µM |
|---|---|---|---|---|---|
| LhG4-mGR driver | S7 | | | | 20 |
| pHTOP::FT | COF3-12 | | 20 | 20 | 16.5 |
| | COF7-30 | | 20 | 19 | 14.85714 |
| wild type | Col | 20 | | | 20 |

Spraying with 30 mM inducer has reduced time to flowering by up to 6 days compared to both non-transgenic or non-sprayed plants.

FIG. 12 also illustrates consequences of spraying.

In place of the GUS reporter in the pHTOP-FT construct, another gene can be used that facilitates floral transition by affecting meristem identity directly, i.e. LEAFY or AP1, therefore creating a compact system that would provide all necessary and sufficient signals to change the plant from vegetative to floral development.

Ryegrass Transformation System

This invention can be applied to ryegrass *Lolium perenne*, for which we have developed efficient stable transformation system as follows:

Protocol adapted from Altpeter et al 2000, Molecular Breeding 6.

Materials florally induced tillers of *Lolium perenne*
Na-hypochlorite (5% available chlorine)
sterile ddH2O
100 mm Petri plates containing LP5 medium*
100 mm Petri plates containing LP3-OS medium
100 mm Petri plates containing LP3 medium
100 mm Petri plates containing LP3 medium+200 mg/L Hygromycin (Hm)
100 mm Petri plates containing MSK medium+200 mg/L Hm
250 ml culture vessels containing MSO medium+200 mg/L
Hygromycin stock solution (50 mg/ml in PDS, sterile)

Procedure

Harvest and surface sterilise floral tillers of *Lolium perenne* in 5% available chlorine Na-hypochlorite for 15 minutes using a Mason jar (or equivalent) under constant agitation.
Rinse tillers with autoclaved ddH2O.
Aseptically dissect floral meristems.
Culture meristems on callus induction medium LP5 (16-20 explants per plate) and incubate in the dark for four to six weeks.
On the day of transformation transfer embryogenic callus material to high osmotic medium LP3-OS. Arrange approximately 4 cm2 of calli in the centre of the Petri dish.
Incubate calli for 4-6 hours at room temperature.
Prepare particles and perform biolistic transformation following the protocol: "Biolistic Transformation of *Lolium perenne* with the Bio-Rad Particle Delivery System (PDS)". Plasmids are co-transformed. One plasmid (pAcH1) contains the hygromycin phosphotransferase gene conferring resistance to the antibiotic hygromycin expressed from the rice actin promoter and the second plasmid contains the genetic construct of interest for transformation. Plasmids are mixed in a one to one ratio at 1 µg/µL and simultaneously coated onto the microcarriers.
Incubate bombarded calli on high osmotic medium LP3-OS for an additional 12-16 hours (overnight) at 25° C. in the dark.
Transfer bombarded calli to LP3 medium and incubate for 48 hours at 25° C. in the dark.
Plate calli on selection medium (LP3+200 mg/l Hygromycin (Hm)). Incubate at 25° C. in the dark on selection medium for two weeks.
Transfer all Hm-resistant callus material to regeneration medium MSK+200 mg/l Hm and incubate for four weeks at 25° C. under a 16 hour photoperiod.
Transfer developed shoots to MS0+200 mg/l Hm and incubate for another two to four weeks at 25° C. under 16 hour photoperiod.
Screen by PCR Hm-resistant plants growing on MSO+200 mg/L Hm.
Microprojectile bombardment of *Lolium perenne* with the Bio-Rad Particle Delivery System (PDS-1000/He)
Taken from the PDS-100/He manual. These procedures were developed by Sanford et al. (1992).

Materials and Solutions

Bio-Rad Biolistic® PDS-1000/He Particle Delivery System
Rupture disks (900 PSI)
Macrocarriers
Macrocarrier holders
Microcarriers (1.0 µm)
Stopping screens
Autoclaved 1.5 ml eppendorf tubes
Micropipette tips
Vortex and microfuge
Torque wrench tool
Pen vac
70% Ethanol
Absolute Ethanol
2.5 M CaCl2
100 mM Spermidine (A) Microcarrier Preparation For 120 bombardments using 500 µg per bombardment.
1. In a 1.5 ml microfuge tube, weigh out 60 mg of microparticles.
2. Add 1 ml of 70% ethanol, freshly prepared.
3. Vortex on a platform vortexer for 3-5 minutes.
4. Incubate for 15 minutes.
5. Pellet the microparticles by spinning for 5 seconds in a microfuge.
6. Remove the liquid and discard.
7. Repeat the following steps three times:
   a. Add 1 ml of sterile water
   b. Vortex for 1 minute
   c. Allow the particles to settle for 1 minute
   d. Pellet the microparticles by spinning for 2 seconds in a microfuge.
   e. Remove the liquid and discard.
8. Add sterile 50% glycerol to bring the microparticle concentration to 60 mg/ml (assume no loss during preparation).
9. Store the microparticles at room temperature for up to 2 weeks.

(B) Coating DNA onto Microcarriers

The following procedure is sufficient for six bombardments; if fewer bombardments are needed, prepare enough microcarriers for three bombardments by reducing all volumes by one half. When removing aliquots of microcarriers, it is important to vortex the tube containing the microcarriers continuously in order to maximise uniform sampling.
1. Vortex the microcarriers prepared in 50% glycerol (60 mg/ml) for 5 minutes on a platform vortexer to resuspend and disrupt agglomerated particles.
2. Remove 50 µl (3 mg) of microcarriers to a 1.5 ml microfuge tube.
3. While vortexing vigorously, add in order:
   5 µl DNA (1 µg/µl)
   50 µl CaCl2 (2.5 M)
   20 µl spermidine (0.1 M)
4. Continue vortexing for 2-3 minutes
5. Allow the microcarriers to settle for 1 minute
6. Pellet the microcarriers by spinning for 2 seconds in a microfuge
7. Remove the liquid and discard
8. Add 140 µl of 70% ethanol without disturbing the pellet
9. Remove the liquid and discard
10. Add 140 µl of 100% ethanol without disturbing the pellet
11. Remove the liquid and discard
12. Add 48 µl of 100% ethanol
13. Gently resuspend the pellet by tapping the side of the tube several times, and then by vortexing at low speed for 2-3 seconds
14. Remove six 6 µl aliquots of microcarriers and transfer them to the centre of a macrocarrier. An effort is made to remove equal amounts (500 µg) of microcarriers each time and to spread them evenly over the central 1 cm of the macrocarrier using the pipette tip. Desiccate immediately.

C) Bombardment Procedure

Open valve of helium cylinder.

Adjust helium regulator by turning the helium pressure regulator to 200 PSI above chosen rupture disk (e.g. if a 900 PSI rupture disk will be used, the working pressure has to be adjusted to 1100 PSI).

Turn on vacuum pump.

Place 900 psi rupture disk in the rupture disk-retaining cap. Screw on and tighten retaining cap.

Place macrocarriers in sterile macrocarrier holder.

Place stop screen and macrocarrier holder in the launch assembly, tighten screw lid and place below rupture disk-retaining cap. Launch assembly should be set to a Gap distance of ¼ inch and macrocarrier travel distance of 11 mm.

Place tissue sample at a target distance of 90 mm.

Turn on main switch of PDS.

Apply vacuum to 27 inches of Hg.

Hold vacuum and press "fire" button until shot is performed (automatic).

Release "fire" button and vent chamber.

After shooting close valve of helium cylinder and loosen pressure valve.

Culture Media

Weights and volumes required of each individual ingredient are specified in Table 1. Adjust media pH to 5.8 with KOH. The addition of a solidifng agent is required. Use agarose (for LP3, LP5 and LP3-OS) and 0.8% (w/v) Agar for MS0 and MSK prior to sterilising. Media LP3, LP5 and MSK are modified from Murashige and Skoog (1962)

We have shown that ryegrass plants having a construct overexpressing the *arabidopsis* gene show accelerated floral transition as compared to the non-transformed plants, as shown in FIG. 5.

Those skilled in the art will appreciate that the invention described above is susceptible to variations and modifications other than those specifically described. It is to be understood that the invention includes all such variations and modifications. The invention also includes all of the steps, features, compositions and products referred to or indicated in this specification, individually or collectively, and any and all combinations of two or more of said steps or features.

REFERENCES

1 Davis, S. J. (2002) Photoperiodism: the coincidental perception of the season. *Curr Biol* 12 (24), R841-843

TABLE 1

Compositions of the media used

| Media component | LP3 | LP5 | LP3-OS | MSK | MS0 |
|---|---|---|---|---|---|
| Macro elements (mg/l final concentration) | | | | | |
| KNO3 | 1900 | 1900 | 1900 | 1900 | 1900 |
| NH4NO3 | 1650 | 1650 | 1650 | 1650 | 1650 |
| CaCl2 × 2H2O | 440 | 440 | 440 | 440 | 440 |
| MgSO4 × 2H2OKH2PO4 | 370 | 370 | 370 | 370 | 370 |
| KCl | 170 | 170 | 170 | 170 | 170 |
| Micro elements (mg/l final concentration) | | | | | |
| Na2EDTA | 37.3 | 37.3 | 37.3 | 37.3 | 37.3 |
| FeSO4 × 7H2O | 27.8 | 27.8 | 27.8 | 27.8 | 27.8 |
| H3BO3 | 6.2 | 6.2 | 6.2 | 6.2 | 6.2 |
| KI | 0.83 | 0.83 | 0.83 | 0.83 | 0.83 |
| MnSO4 × H2O | 16.9 | 16.9 | 16.9 | 16.9 | 16.9 |
| ZnSO4 × 7H2O | 8.6 | 8.6 | 8.6 | 8.6 | 8.6 |
| CuSO4 × 5H2O | 0.025 | 0.025 | 0.025 | 0.025 | 0.025 |
| Na2MoO4 × 2H2O | 0.25 | 0.25 | 0.25 | 0.25 | 0.25 |
| CoCl2 × 6H2O | 0.025 | 0.025 | 0.025 | 0.025 | 0.025 |
| Carbohydrates (g/l final concentration) | | | | | |
| Maltose | 30 | 30 | 30 | 30 | 30 |
| D-Mannitol | | | 64 | | |
| Hormones (mg/l final concentration) | | | | | |
| 2,4-D | 3.0 | 5.0 | 3.0 | | |
| Kinetin | | | | 0.2 | |
| Vitamins (mg/l final concentration) | | | | | |
| Pyridoxine HCl | 0.5 | 0.5 | 0.5 | 0.5 | |
| Thiamine HCl | 0.1 | 0.1 | 0.1 | 0.1 | |
| Nicotinic acid | 0.5 | 0.5 | 0.5 | 0.5 | |
| Myo-Inositol | 100 | 100 | 100 | 100 | |
| Other organics (mg/l final concentration) | | | | | |
| Glycine | 2 | 2 | 2 | 2 | 2 |

2 Araki, T. (2001) Transition from vegetative to reproductive phase. *Curr Opin Plant Biol* 4 (1), 63-68.
3 Reeves, P. H. and Coupland, G. (2000) Response of plant development to environment: control of flowering by day-length and temperature. *Current Opinion in Plant Biology* 3 (1), 37-42
4 Colasanti, J. and Sundaresan, V. (2000) 'Florigen' enters the molecular age: long-distance signals that cause plants to flower. *Trends Biochem Sci* 25 (5), 236-240.
5 Kardailsky, I. et al. (1999) Activation Tagging of the Floral Inducer FT. *Science* 286 (5446), 1962-1965
6 Kobayashi, Y. et al. (1999) A Pair of Related Genes with Antagonistic Roles in Mediating Flowering Signals. *Science* 286 (5446), 1960-1962
7 Weigel, D. and Kardailsky, I. (2001) Flowering locus T (FT) and genetically modified plants having modulated flower development. U.S. Pat. No. 6,225,530 The Salk Institute for Biological Studies (La Jolla, Calif.)
8 Yanofsky, M. and Weigel, D. (1997) SEED PLANTS EXHIBITING EARLY REPRODUCTIVE DEVELOPMENT AND METHODS OF MAKING SAME. Patent WO9746077 UNIV CALIFORNIA (US)
9 Weigel, D. (1998) Genetically modified plants having modulated flower development. U.S. Pat. No. 5,844,119 The Salk Institute for Biological Studies (San Diego, Calif.)
10 Yano, M. et al. (2001) Genetic control of flowering time in rice, a short-day plant. *Plant Physiol* 127 (4), 1425-1429
11 Kojima, S. et al. (2002) Hd3a, a rice ortholog of the *Arabidopsis* FT gene, promotes transition to flowering downstream of Hd1 under short-day conditions. *Plant Cell Physiol* 43 (10), 1096-1105
12 Yano, M. et al. (2000) Hd1, a major photoperiod sensitivity quantitative trait locus in rice, is closely related to the *Arabidopsis* flowering time gene CONSTANS. *Plant Cell* 12 (12), 2473-2484.
13 Takahashi, Y. et al. (2001) Hd6, a rice quantitative trait locus involved in photoperiod sensitivity, encodes the alpha subunit of protein kinase CK2. *Proc Natl Acad Sci USA* 98 (14), 7922-7927
14 Hayama, R. et al. (2003) Adaptation of photoperiodic control pathways produces short-day flowering in rice. *Nature* 422 (6933), 719-722
15 Frohman, M. A. et al. (1988) Rapid production of full-length cDNAs from rare transcripts: amplification using a single gene-specific oligonucleotide primer. *Proc Natl Acad Sci USA* 85 (23), 8998-9002
16 Ohara, O. et al. (1989) One-sided polymerase chain reaction: the amplification of cDNA. *Proc Natl Acad Sci USA* 86 (15), 5673-5677
17 Loh, E. Y. et al. (1989) Polymerase chain reaction with single-sided specificity: analysis of T cell receptor delta chain. *Science* 243 (4888), 217-220
18 Aoyama, T. and Chau, N. H. (1997) A glucocorticoid-mediated transcriptional induction system in transgenic plants. *Plant J* 11 (3), 605-612
19 Moore, I. et al. (1998) A transcription activation system for regulated gene expression in transgenic plants. *Proc Natl Acad Sci USA* 95 (1), 376-381.
20 Caddick, M. X. et al. (1998) An ethanol inducible gene switch for plants used to manipulate carbon metabolism. *Nat Biotechnol* 16 (2), 177-180.
21 Roslan, H. A. et al. (2001) Characterization of the ethanol-inducible alc gene-expression system in *Arabidopsis thaliana*. *Plant J* 28 (2), 225-235
22 De Veylder, L. et al. (1997) Herbicide safener-inducible gene expression in *Arabidopsis thaliana*. *Plant Cell Physiol* 38 (5), 568-577
23 Bradley, D. J. et al. (1997) Inflorescence commitment and architecture in *Arabidopsis*. *Science* 275 (5296), 80-83
24 Bradley, D. et al. (1997) Flowering genes. Patent WO9710339
25 Ratcliffe, O. J. et al. (1998) A common mechanism controls the life cycle and architecture of plants. *Development* 125 (9), 1609-1615
26 Jensen, C. S. et al. (2001) A Terminal Flower1-Like Gene from Perennial Ryegrass Involved in Floral Transition and Axillary Meristem Identity. *Plant Physiol* 125 (3), 1517-1528.
27 Schoof, H. et al. (2000) The stem cell population of *Arabidopsis* shoot meristems in maintained by a regulatory loop between the CLAVATA and WUSCHEL genes. *Cell* 100 (6), 635-644

---

The invention claimed is:

1. A substantially purified or isolated nucleic acid comprising a nucleotide sequence selected from the group consisting of:
   (a) SEQ ID NO: 1;
   (b) a nucleic acid encoding the amino acid sequence of SEQ ID NO: 26 or 27;
   (c) a sequence that is the complement of SEQ ID NO:1;
   (d) a sequence that is the complement of the nucleic acid sequence of (b); and
   (e) an RNA sequence corresponding to the sequence recited in (a), (b), (c), or (d).

2. A construct comprising one or more nucleic acids according to claim 1.

3. The construct according to claim 2 wherein the one or more nucleic acids are operably linked to one or more regulatory elements, such that the one or more nucleic acids are each expressed.

4. The construct according to claim 3, wherein the one or more regulatory elements include a promoter and a terminator, said promoter, nucleic acid and terminator being operably linked.

5. A plant cell, plant, plant seed or other plant part, comprising the construct according to claim 2.

6. A plant, plant seed or other plant part derived from the plant cell or plant according to claim 5, wherein the plant, plant seed or other plant part contains the construct.

7. A method of modifying flowering in a plant, said method comprising the step of introducing into said plant an effective amount of the nucleic acid according to claim 1, or the construct according to claim 2.

8. The method according to claim 7 wherein the method results in the induction of more than one gene encoding a protein involved in the regulation of flowering.

9. The method according to claim 7 wherein floral development is activated or accelerated in the plant.

10. A preparation for transforming a plant comprising the nucleic acid according to claim 1, or the construct according to claim 2.

11. The substantially purified or isolated nucleic acid of claim 1, comprising SEQ ID NO:1.

12. The substantially purified or isolated nucleic acid of claim 1, comprising a nucleic acid encoding the amino acid sequence of SEQ ID NO:26 or 27.

* * * * *